United States Patent [19] [11] Patent Number: 5,037,841
Schohe et al. [45] Date of Patent: Aug. 6, 1991

[54] 1,3-DISUBSTITUTED PYRROLIDINES

[75] Inventors: Rudolf Schohe, Wuppertal; Peter-Rudolf Seidel, Cologne; Jörg Traber, Lohmar; Thomas Glaser, Roesrath, all of Fed. Rep. of Germany

[73] Assignee: Bayer Aktiengesellschaft, Leverkusen, Fed. Rep. of Germany

[21] Appl. No.: 336,977

[22] Filed: Apr. 12, 1989

[30] Foreign Application Priority Data

Apr. 19, 1988 [DE] Fed. Rep. of Germany ....... 3812989
Oct. 15, 1988 [DE] Fed. Rep. of Germany ....... 3835291

[51] Int. Cl.$^5$ ................. A61K 31/425; C07D 417/08; C07D 209/04; C07D 239/02
[52] U.S. Cl. ................................. 514/373; 514/256; 514/307; 514/309; 514/312; 514/314; 514/338; 514/339; 514/343; 514/372; 514/375; 514/378; 514/403; 514/424; 514/428; 544/315; 544/319; 544/333; 546/139; 546/141; 546/148; 546/152; 546/157; 546/165; 546/270; 546/273; 546/275; 546/280; 548/207; 548/210; 548/214; 548/221; 548/240; 548/243; 548/371; 548/470; 548/491; 548/524
[58] Field of Search ....................... 544/315, 319, 333; 546/139, 141, 148, 152, 157, 165, 270, 273, 275, 280; 548/207, 210, 214, 221, 240, 243, 371, 470, 491, 524

[56] References Cited

U.S. PATENT DOCUMENTS 3,577,432 5/1971 Helsley et al. ...................... 548/538
3,642,803 2/1972 Welstead, Jr. ...................... 546/201

FOREIGN PATENT DOCUMENTS 252353 1/1988 European Pat. Off. .
1964510 7/1970 Fed. Rep. of Germany .
1964511 7/1970 Fed. Rep. of Germany .
2315092 10/1973 Fed. Rep. of Germany .

OTHER PUBLICATIONS

Duncan et al, "Synthesis and Biological Properties . . . ", J. Med. Chem. 12(3) 442–4 (1969).

Meul et al, "Preparation of 4-Benzylox-3-Pyrroli . . . ", CA 108:167294j (1988).
Chemical Abstracts, vol. 102, No. 16, Apr. 22, 1985, p. 376.
Chemical Abstracts, vol. 82, No. 21, May 26, 1975, p. 611.
Chemical Abstracts, vol. 81, No. 25, Dec. 23, 1974, p. 36.
Chemical Abstracts, vol. 77, No. 25, Dec. 18, 1972, pp. 400–401.
Chemical Abstracts, vol. 70, No. 15, Apr. 14, 1969, pp. 356–357.
Chemical Abstracts, vol. 67, No. 25, Dec. 18, 1967, p. 10884.
Chemical Abstracts, vol. 71, No. 3, Jul. 21, 1969, p. 311.

*Primary Examiner*—C. Warren Ivy
*Assistant Examiner*—Celia Chang
*Attorney, Agent, or Firm*—Sprung Horn Kramer & Woods

[57] ABSTRACT

Novel 1,3-disubstituted pyrrolidines active on the central nervous system of the formula

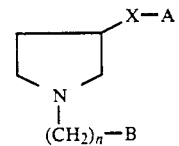

wherein
A denotes phenyl or hetaryl, which is optionally fused with aromatic, saturated or unsaturated cyclic or heterocyclic hydrocarbons, where this radical can optionally be substituted,
X denotes —O—$CH_2$—, —$CH_2$—O— or —O—,
n denotes a number from 1 to 19, and
B denotes cyano or a group of the formula —$COOR^1$, —$CONR^2R^3$, —$SO_2NR^2R^3$, —$SO_mR^4$, —$NR^5R^6$, or —C≡C—$CH_2$—$NR^5R^6$,
and salts thereof.

9 Claims, No Drawings

1,3-DISUBSTITUTED PYRROLIDINES

The invention relates to 1,3-disubstituted pyrrolidines, processes for their preparation and their use in medicaments.

Specific pyrrolidines having action on the central nervous system have been disclosed in DE-A 1,964,510. In particular, 1-substituted 3-phenoxypyrrolidines which have a pharmacological action on the central nervous system are described in DE-A 1,964,511. The compounds have muscle relaxant properties (page 3, 1st paragraph).

From U.S. Pat. No. 3,642,803, 1-[2-(indol-3-yl)-ethyl]-3-(2-methoxy-phenoxy)pyrrolidine is known which likewise has an action on the central nervous system.

In DE-A 2,315,092, pyrrolidines having antipsychotic and muscle relaxant action are likewise described.

New 1,3-disubstituted pyrrolidines of the general formula (I)

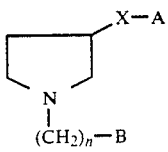

wherein

A denotes phenyl or hetaryl, which is optionally fused with aromatic, saturated or unsaturated cyclic or heterocyclic hydrocarbons, where this radical can optionally be substituted, X denotes —O—CH$_2$—, —CH$_2$—O— or —O—, and B denotes cyano or a group of the formula —COOR$^1$, —CONR$^2$R$^3$, —SO$_2$NR$^2$R$^3$, —SO$_m$R$^4$, —NR$^5$R$^6$, or —C≡C—CH$_2$—NR$^5$R$^6$ where R$^1$ stands for hydrogen, alkyl, cycloalkyl, alkenyl, aryl or aralkyl, R$^2$ and R$^3$ are identical or different and stand for hydrogen, alkyl, cycloalkyl, aryl or aralkyl, where the aryl radicals can be substituted by halogen, alkoxy or alkoxycarbonyl, R$^4$ stands for alkyl, cycloalkyl, aryl or aralkyl, where the aryl radicals can be monosubstituted, disubstituted or trisubstituted by identical or different halogen, cyano, alkyl, alkoxy, trifluoromethyl or trifluoromethoxy, or for a group of the formula

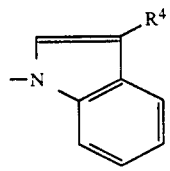

wherein R$^4$, denotes hydrogen or alkyl, stands for a number 0, 1 or 2,

R$^5$ and R$^6$ are identical or different and stand for hydrogen, alkyl, cycloalkyl, aryl or aralkyl, where the aryl radicals can be substituted by halogen, cyano, alkyl, alkoxy or trifluoromethyl, or stand for a group of the formula —COR$^7$ or —SO$_2$R$^8$, wherein R$^7$ denotes hydrogen or a group NHR$^9$ or alkyl, cycloalkyl or alkoxy, or aryl, aryloxy, aralkyl, aralkoxy or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino, R$^8$ denotes cycloalkyl or alkyl which can be substituted by cyano, halogen, alkoxy or alkoxycarbonyl, or aryl, aralkyl or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, nitro, amino, alkylamino or dialkylamino, or denotes a group NR$^2$R$^3$, where R$^2$ and R$^3$ have the abovementioned meanings and R$^9$ denotes hydrogen or cycloalkyl or optionally substituted alkyl or aryl, aralkyl or heteroaryl, where the aryl radicals can be monosubstituted, disubstituted or trisubstituted by identical or different alkyl, alkoxy, alkylthio, halogen, cyano, trifluoromethyl, trifluoromethoxy, trifluoromethylthio, nitro, amino, alkylamino or dialkylamino, or where R$^5$ and R$^6$, together with the nitrogen atom, form a ring from the series comprising

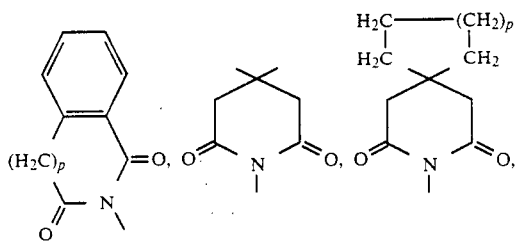

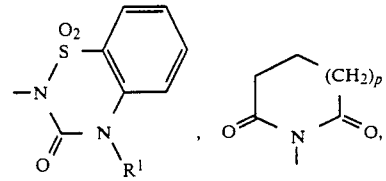

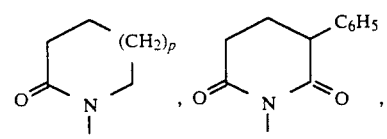

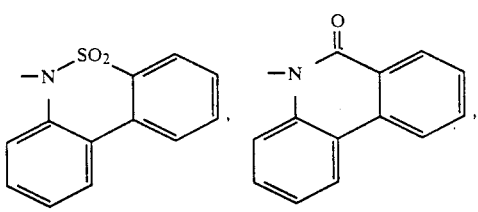

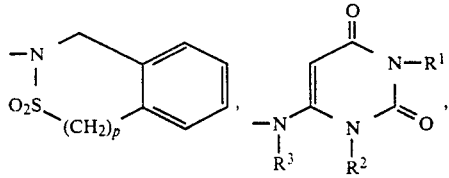

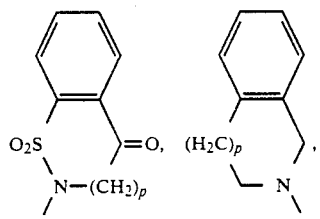

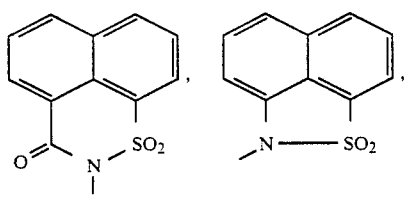

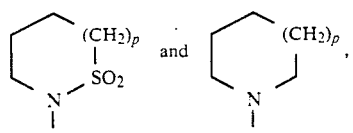

wherein
p denotes a number 0, 1 or 2,
$R^1$, $R^2$ and $R^3$ have the abovementioned meanings, and
n denotes a number from 1 to 10,
and their salts, have been found.

The substances according to the invention surprisingly show a superior action on the central nervous system and can be used for therapeutic treatment in humans and animals.

The substances according to the invention have several asymmetric carbon atoms and can therefore exist in various stereochemical forms. Moreover, compounds having a sulphoxide group can likewise exist in different stereochemical forms. The invention relates both to the individual isomers and to their mixtures. For example, the following isomeric forms of the 1,3-disubstituted pyrrolidines may be mentioned:

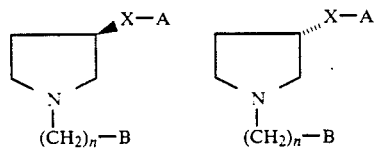

The 1,3-disubstituted pyrrolidines according to the invention can also exist in the form of their salts. In general, salts with inorganic or organic acids may be mentioned here.

In the context of the present invention, physiologically acceptable salts are preferred. Physiologically acceptable salts of the 1,3-disubstituted pyrrolidines can be salts of the substances according to the invention with mineral acids, carboxylic acids or sulphonic acids. For example, hydrochloric acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, oxalic acid, malonic acid, succinic acid, maleic acid, fumaric acid, malic acid, tartaric acid, citric acid or benzoic acid are preferred.

The radical A can be a phenyl or hetaryl radical which is optionally fused with aromatic, saturated, unsaturated or cyclic hydrocarbons or heterocycles. A hetaryl radical in the context of the invention is in general a monocyclic 5- or 6-membered ring having one or two, preferably one, nitrogen, oxygen or sulphur atom as heteroatom. For example, pyrrolyl, furyl, thienyl, oxazolyl, thiazolyl, isoxazolyl, isothiazolyl, pyridyl, pyranyl, thiopyranyl, pyridazinyl, pyrimidinyl and pyrazinyl may be mentioned.

Further rings can be fused onto the phenyl and hetaryl rings.

Aromatic rings which may be mentioned are aryl ($C_6$ to $C_{12}$), preferably phenyl.

Unsaturated rings which may be mentioned are five to eight, preferably five- or six-membered hydrocarbons having one or two, preferably one, double bond. For example, cyclopentene may be mentioned.

Saturated rings which may be mentioned are 4- to 8-membered, cyclic hydrocarbons, preferably cyclopentyl and cyclohexyl.

Radicals A which may be mentioned, for example, are: phenyl, 2-fluorophenyl, 2-methylphenyl, 2-methoxyphenyl, 3-methoxyphenyl, 4-methoxyphenyl, 2-cyano-6-methoxyphenyl, alkenyloxyphenyl, 2-aminocarbonylphenyl, 1-naphthyl, 2-naphthyl, 1-tetralyl, 4-indolyl, 1-isoquinolyl, 2-quinolyl and 8-quinolyl.

Alkyl in general stands for a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl in general stands for a straight-chain or branched hydrocarbon radical having 2 to 12 carbon atoms and one or more, preferably one or two, double bonds. The lower alkyl radical having 2 to about 6 carbon atoms and one double bond is preferred. An alkenyl radical having 2 to 4 carbon atoms and one double bond is particularly preferred. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

Cycloalkyl in general stands for a cyclic hydrocarbon radical having 5 to 8 carbon atoms. The cyclopentane and the cyclohexane ring are preferred. Examples which may be mentioned are cyclopentyl, cyclohexyl, cycloheptyl and cyclooctyl.

Aryl in general stands for an aromatic radical having 6 to about 12 carbon atoms. Preferred aryl radicals are phenyl, naphthyl and biphenyl.

Aralkyl in general stands for an aryl radical having 7 to 14 carbon atoms bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl.

Alkoxy in general stands for a straight-chain or branched hydrocarbon radical having 1 to 12 carbon atoms bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Aryloxy in general stands for an aromatic radical having 6 to about 12 carbon atoms which is bonded via an oxygen atom. Preferred aryloxy radicals are phenoxy or naphthyloxy.

Aralkoxy in general stands for an aralkyl radical having 7 to 14 carbon atoms, where the alkylene chain is bonded via an oxygen atom. Aralkoxy radicals having 1 to 6 carbon atoms in the aliphatic moiety and 6 to 12 carbon atoms in the aromatic moiety are preferred. Examples which may be mentioned are the following aralkoxy radicals: benzyloxy, naphthylmethoxy, phenethoxy and phenylpropoxy.

Alkylthio in general stands for a straight-chain or branched hydrocarbon radical having 1 to 12 carbon atoms bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio.

Acyl in general stands for phenyl or straight-chain or branched lower alkyl having 1 to about 6 carbon atoms which are bonded via a carbonyl group. Phenyl and alkyl radicals having up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Alkoxycarbonyl can, for example, be represented by the formula

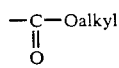

Alkyl in this case stands for a straight-chain or branched hydrocarbon radical having 1 to 12 carbon atoms. Lower alkoxycarbonyl having 1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: methoxycarbonyl, ethoxycarbonyl, propoxycarbonyl, isopropoxycarbonyl, butoxycarbonyl and isobutoxycarbonyl.

Heteroaryl in the context of the abovementioned definition in general stands for a 5- to 6-membered aromatic ring which can contain oxygen, sulphur and/or nitrogen as heteroatoms and onto which a further aromatic ring can be fused. 5- and 6-membered aromatic rings which contain one oxygen, one sulphur and/or up to 2 nitrogen atoms and which are optionally fused onto benzene, and their N-oxides are preferred. The following heteroaryl radicals may be mentioned as particularly preferred: thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benozoxazolyl, isoxazolyl, imidazolyl, benzimidazolyl, pyrazolyl and indolyl.

Halogen in general stands for fluorine, chlorine, bromine or iodine, preferably for fluorine, chlorine or bromine. Halogen particularly preferably stands for fluorine or chlorine.

Alkylsulphonyl can, for example, denote ethylsulphonyl, methylsulphonyl, 3-chloropropyl-sulphonyl and 4-chlorobutyl-sulphonyl.

Arylsulphonyl can, for example, denote phenylsulphonyl, 4-nitrophenylsulphonyl, 1-naphthylsulphonyl, 2-naphthylsulphonyl or 2,4-dichlorophenylsulphonyl.

Alkylarylsulphonyl can, for example, denote 4-methyl-phenylsulphonyl.

Aralkylsulphonyl can, for example, denote phenylmethylsulphonyl.

The radicals mentioned can, of course, be substituted by further radicals, for example lower alkyl ($C_1$ to about $C_6$), lower alkoxy ($C_1$ to about $C_6$), halogen (in particular fluorine and chlorine) or aryl (in particular phenyl), cyano or alkoxy-($C_4$ to $C_6$)-carbonyl.

1,3-Disubstituted pyrrolidines of the general formula (I) are preferred wherein

A stands for phenyl or a monocyclic five- or six-membered hetaryl radical which contains one or two nitrogen and/or oxygen and/or sulphur atoms, onto which are optionally fused one to three aromatic ($C_5$ to $C_8$), saturated or unsaturated cyclic ($C_5$ to $C_8$) hydrocarbons or five- or six-membered heterocycles (having one or two nitrogen and/or oxygen and/or sulphur atoms), where this radical is optionally monosubstituted or disubstituted by lower alkyl, lower alkoxy, lower alkoxycarbonyl, lower alkenyloxy, acyloxy, benzoyloxy, cyano, phenyl, benzyl, fluorine, chlorine, bromine, trifluoromethyl, trifluoromethoxy, difluoromethoxy or a radical of the formula —CO—NYZ, —NH—SO$_2$—Y', —SO$_2$—NYZ or —NH—CO—Y, where Y and Z are identical or different and stand for hydrogen or alkyl ($C_1$ to $C_6$), and Y' stands for alkyl ($C_1$ to $C_6$) or aryl, and in the case of nitrogen heterocycles is optionally present as the N-oxide, X stands for —CH$_2$—O—, —O—CH$_2$— or —O—, B stands for cyano or a group of the formula —COOR$^1$, CONR$^2$R$^3$, —SO$_2$NR$^2$R$^3$, —SO$_m$R$^4$, NR$^5$R$^6$ or —C≡C—CH$_2$—NR$^5$R$^6$, where R$^1$ stands for hydrogen, alkyl ($C_1$ to $C_{11}$), cycloalkyl ($C_5$ to $C_8$), alkenyl ($C_2$ to $C_{12}$), aryl ($C_6$ to $C_{12}$) or aralkyl ($C_7$ to $C_{17}$), R$^2$ and R$^3$ are identical or different and stand for hydrogen, alkyl ($C_1$ to $C_{12}$), cycloalkyl ($C_5$ to $C_8$), aryl ($C_6$ to $C_{12}$) or aralkyl ($C_7$ to $C_{14}$), where the aryl radicals can be substituted by halogen, alkoxy or alkoxycarbonyl ($C_1$-$C_6$), R$^4$ stands for alkyl ($C_1$ to $C_{12}$), cycloalkyl ($C_5$ to $C_8$), aryl ($C_6$ to $C_{12}$) or aralkyl ($C_7$ to $C_{14}$), where the aryl radicals can be monosubstituted, disubstituted or trisubstituted by identical or different halogen, cyano, alkyl ($C_1$ to $C_6$), alkoxy ($C_1$ to $C_6$), trifluoromethyl or trifluoromethoxy, or for a group of the formula

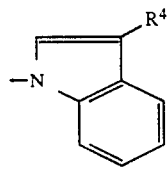

wherein $R^{4'}$ denotes hydrogen or alkyl ($C_1$–$C_6$) or
m stands for a number 0, 1 or 2, $R^5$ and $R^6$ are identical or different and stand for hydrogen, alkyl ($C_1$ to $C_{12}$), cycloalkyl ($C_5$ to $C_8$), aryl ($C_6$ to $C_{12}$) or aralkyl ($C_7$ to $C_{14}$), where the aryl radicals can be substituted by halogen, cyano, alkyl ($C_1$ to $C_6$), alkoxy ($C_1$ to $C_6$) or trifluoromethyl, or stands for a group of the formula —$COR^7$ or —$SO_2R^8$ wherein $R^7$ denotes hydrogen or a group $NHR^9$ or alkyl ($C_1$ to $C_{11}$), cycloalkyl ($C_5$ to $C_8$) or alkoxy ($C_1$ to $C_{12}$), or aryl ($C_6$ to $C_{12}$), aryloxy ($C_6$ to $C_{12}$), aralkyl ($C_7$ to $C_{14}$), aralkoxy ($C_6$ to $C_{12}$) or heteroaryl (five- or six-membered ring having one or two oxygen and/or nitrogen and/or sulphur atoms), where the radicals mentioned can be monosubstituted, disubstituted or trisubstituted by identical or different alkyl ($C_1$ to $C_6$), alkoxy ($C_1$ to $C_6$), alkylthio ($C_1$ to $C_6$), halogen, cyano, trifluoromethyl, trifluoromethoxy, trifluoromethylthio, amino, alkyl-($C_1$ to $C_6$)-amino or dialkyl-($C_1$ to $C_6$)-amino, $R^8$ denotes cycloalkyl ($C_5$ to $C_8$), or alkyl ($C_1$ to $C_{12}$) which can be substituted by cyano, halogen, alkoxy ($C_1$ to $C_{12}$) or alkoxy-($C_1$ to $C_{12}$)-carbonyl or aryl ($C_6$ to $C_{12}$), aralkyl ($C_7$ to $C_{14}$) or heteroaryl (five- or six-membered ring having one or two oxygen and/or nitrogen and/or sulphur atoms), where the radicals mentioned can be monosubstituted, disubstituted or trisubstituted by identical or different alkyl ($C_1$ to $C_6$), alkoxy ($C_1$ to $C_6$), alkylthio ($C_1$ to $C_6$), halogen, cyano, trifluoromethyl, trifluoromethoxy, trifluoromethylthio, nitro, amino, alkyl-($C_1$ to $C_6$)-amino or dialkyl-($C_1$ to $C_6$)-amino or denotes a group $NR^2R^3$, wherein $R^2$ and $R^3$ have the abovementioned meanings and $R^9$ denotes hydrogen, or cycloalkyl ($C_5$ to $C_8$), or optionally substituted alkyl ($C_1$ to $C_{12}$), or aryl ($C_6$ to $C_{12}$), aralkyl ($C_7$ to $C_{14}$) or heteroaryl (five- or six-membered ring having one or two oxygen and/or nitrogen and/or sulphur atoms), where the aryl radicals can be monosubstituted, disubstituted or trisubstituted by identical or different alkyl ($C_1$ to $C_6$), alkoxy ($C_1$ to $C_6$), alkylthio ($C_1$ to $C_6$), halogen, cyano, trifluoromethyl, trifluoromethoxy, trifluoromethylthio, nitro, amino, alkyl-($C_1$ to $C_6$)-amino or dialkyl-($C_1$ to $C_6$)-amino, or where $R^5$ and $R^{6,}$ together with the nitrogen atom, form a ring from the series comprising

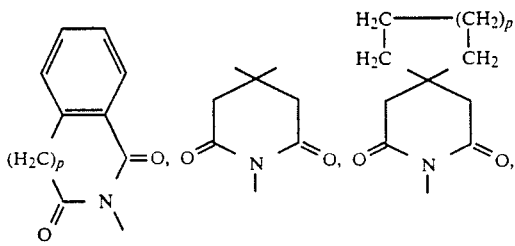

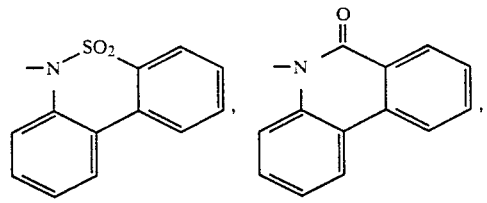

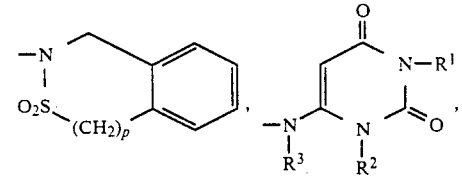

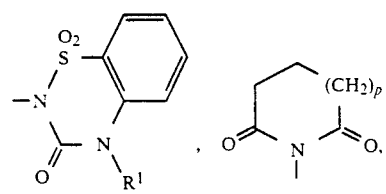

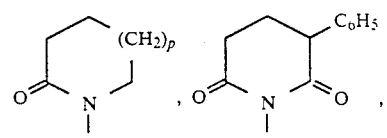

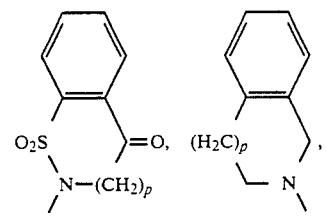

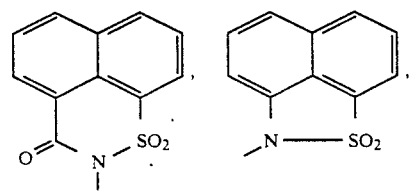

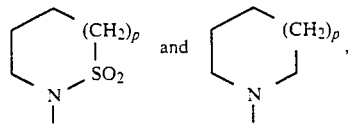

wherein p0 p denotes a number 0, 1 or 2,

R¹, R² and R³ have the abovementioned meanings,
n denotes a number from 1 to 10 and their salts.

Compounds of the general formula (I) are particularly preferred in which

A stands for phenyl or a monocyclic five- or six-membered hetaryl radical which contains one or two nitrogen and/or oxygen and/or sulphur atoms, onto which one to three aromatic ($C_5$ to $C_8$), saturated or unsaturated cyclic ($C_5$ to $C_8$) hydrocarbons or five- or six-membered heterocycles (having one or two nitrogen and/or oxygen and/or sulphur atoms) are optionally fused, where this radical is optionally monosubstituted or disubstituted by lower alkyl, lower alkoxy, lower alkoxycarbonyl, lower alkenyloxy, acyloxy, benzoyloxy, cyano, phenyl, benzyl, fluorine, chlorine, bromine, trifluoromethyl, trifluoromethoxy, difluoromethoxy or a radical of the formula —CO—NYZ, —NH—SO₂—Y', —SO₂—NYZ or NH—Y, where Y and Z are identical or different and stand for hydrogen or alkyl ($C_1$ to $C_6$) and Y' stands for alkyl ($C_1$ to $C_6$) or aryl, and in the case of the nitrogen heterocycles is optionally present as the N-oxide, X stands for —CH₂—O—, —O—CH₂— or —O—, B stands for cyano or a group of the formula —COOR¹, CONR²R³, —SO₂NR²R³, —SO$_m$R⁴, NR⁵R⁶ or —C≡C—CH₂—NR⁵R⁶, where R¹ stands for hydrogen, lower alkyl or phenyl, R² and R³ are identical or different and stand for hydrogen, lower alkyl or phenyl which, in turn, can be substituted by fluorine, chlorine, bromine, lower alkoxy or lower alkoxycarbonyl, R⁴ stands for lower alkyl, or for phenyl which can be monosubstituted or disubstituted by identical or different fluorine, chlorine, bromine, lower alkyl or lower alkoxy, or for a group of the formula

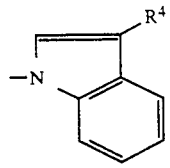

wherein R⁴' denotes hydrogen or lower alkyl, m stands for a number 0, 1 or 2,

R⁵ and R⁶ are identical or different and stand for hydrogen, lower alkyl, phenyl or benzyl, where the phenyl radical can be substituted by fluorine, chlorine, bromine, lower alkyl, lower alkoxy or trifluoromethyl, or stands for a group of the formula —COR⁷ or —SO₂R⁸, wherein R⁷ denotes hydrogen, or denotes a group NHR⁹, or denotes lower alkyl or lower alkoxy, or phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl optionally substituted by lower alkyl, lower alkoxy, fluorine, chlorine, bromine, trifluoromethyl, dimethylamino or diethylamino, R⁸ denotes cyclopropyl, cyclopentyl, cyclohexyl, or lower alkyl which is optionally substituted by cyano, fluorine, chlorine, bromine, trifluoromethyl or lower alkoxycarbonyl, or denotes phenyl, naphthyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl optionally substituted by lower alkyl, lower alkoxy, fluorine, chlorine, bromine, nitro, trifluoromethyl, dimethylamino or diethylamino, or a group NR²R³, where R² and R³ have the abovementioned meanings, and R⁹ denotes lower alkyl which is optionally substituted by cyano, fluorine, chlorine or bromine, or denotes phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl optionally substituted by lower alkyl, lower alkoxy, fluorine, chlorine, bromine, trifluoromethyl, dimethylamino or diethylamino, or R⁵ and R⁶, together with the nitrogen atom, form a ring from the series comprising

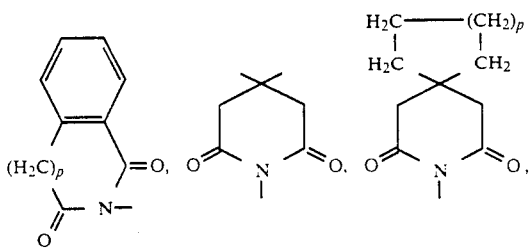

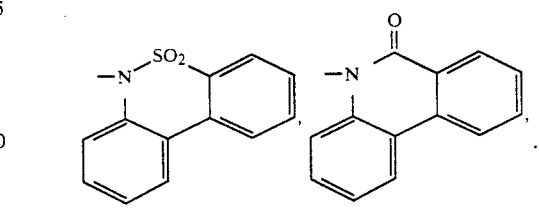

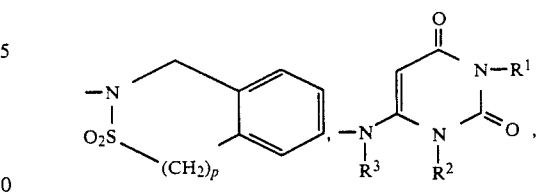

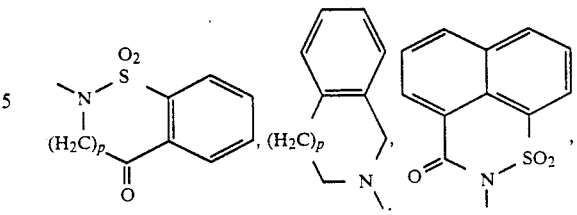

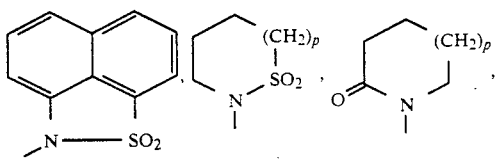

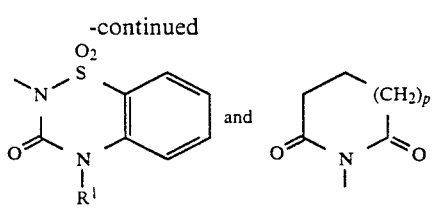 and wherein
p denotes a number 0, 1 or 2,
$R^1$, $R^2$ and $R^3$ have the abovementioned meanings, and
n denotes a number from 1 to 8, and their salts.

Particularly preferred are those compounds of the general formula (I) in which

A stands for phenyl or naphthyl optionally substituted by identical or different lower alkyl, lower alkoxy, lower alkoxycarbonyl, lower alkenyloxy, acyloxy, benzoyloxy, cyano, phenyl, benzyl, sulphonylamino, sulphamoyl ($C_1$ to $C_6$), carbamoyl, carbonylamino, fluorine, chlorine, bromine, trifluoromethyl, trifluoromethoxy or difluoromethoxy, furan, thiophene, isoxazole, pyridine, pyrimidine, indole, indazole, benzofuran, benzisoxazole, quinoline, isoquinoline, tetralin, indene, chroman, dihydrobenzodioxin, dihydroindole, tetrahydroquinoline or dihydrobenzofuran, X stands for —O—$CH_2$—, —$CH_2$—O— or —O—, B stands for cyano, or a group of the formula —$CONR^2R^3$, —$NR^5R^6$, —$SO_mR^4$, —C≡C—$CH_2$—$NR^5R^6$, —$SO_2NR^2R^3$ or $COOR^1$, where $R^1$ denotes hydrogen, methyl, ethyl or phenyl, $R^2$ and $R^3$ are identical or different and denote hydrogen, methyl, ethyl, propyl, isopropyl, butyl or isobutyl or denote phenyl which can be substituted by methoxycarbonyl $R^4$ stands for methyl or ethyl or
for a group of the formula

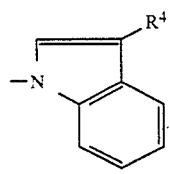

wherein $R^{4'}$ denotes hydrogen or methyl, $R^5$ and $R^6$ are identical or different, and denote hydrogen, methyl, ethyl, propyl, isopropyl, butyl or isobutyl, or
phenyl optionally substituted by fluorine, chlorine, methyl or methoxy, or
denote a group —$COR^7$ or —$SO_2R^8$,
stands for a group $NHR^9$, or for methyl, ethyl, propyl, isopropyl, methoxy, ethoxy, propoxy, isopropoxy or tert.butoxy, or
for phenyl, benzyl, benzyloxy, thienyl, furyl, pyridyl, pyrimidyl, quinolyl or isoquinolyl optionally substituted by methyl, methoxy, fluorine or chlorine, $R^8$ stands for methyl, ethyl, propyl, isopropyl, butyl or isobutyl optionally substituted by fluorine, chlorine, methoxycarbonyl, ethoxycarbonyl, propoxycarbonyl, isopropoxycarbonyl, butoxycarbonyl, isobutoxycarbonyl or tert.-butoxycarbonyl, or
for phenyl, naphthyl, thienyl, furyl, pyridyl, pyrimidyl, quinolyl or isoquinolyl optionally substituted by methyl, ethyl, propyl, isopropyl, methoxy, fluorine, chlorine or nitro, or for a group $NR^2R^3$, where
$R^2$ and $R^3$ have the abovementioned meanings, $R^9$ denotes methyl, ethyl, propyl, isopropyl, butyl, isobutyl, pentyl, isopentyl, hexyl or isohexyl optionally substituted by fluorine or chlorine, or
denotes phenyl which can be substituted by fluorine, chlorine, methyl or methoxy, or $R^5$ and $R^6$ together with the nitrogen atom, form a ring from the series comprising

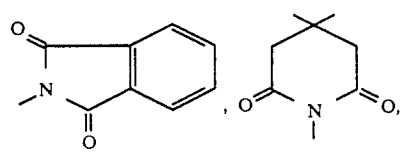

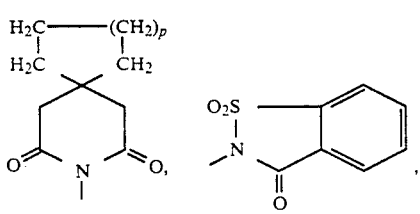

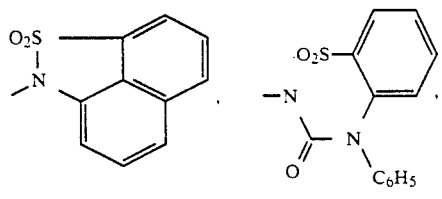

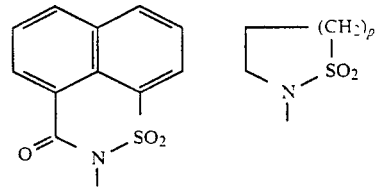

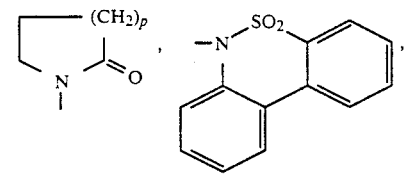

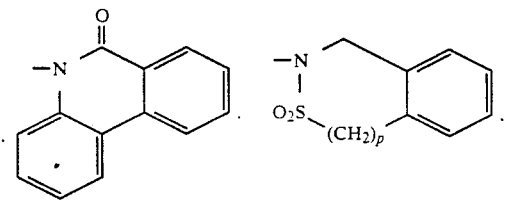

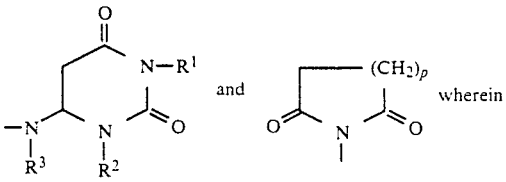

p denotes a number 1 or 2, $R^1$, $R^2$ and $R^3$ have the abovementioned meanings and n denotes a number from 1 to 6, and their salts.

Examples which may be mentioned are the following 1,3-disubstituted pyrrolidines:

3-(2-methoxyphenoxy)-1-[5-(1,1-dioxido-3-oxo-2,3-dihydrobenzisothiazol-2-yl)pentyl]-pyrrolidine
3-(2-methoxyphenoxy)-1-[4-(1,1-dioxido-3-oxo-2,3-dihydrobenzisothiazol-2-yl)butyl]-pyrrolidine
3-(2-methoxyphenoxy)-1-[3-(1,1-dioxido-3-oxo-2,3-dihydrobenzisothiazol-2-yl)propyl]-pyrrolidine
3-(2-methoxyphenoxy)-1-[2-(1,1-dioxido-3-oxo-2,3-dihydrobenzisothiazol-2-yl)ethyl]-pyrrolidine
3-(3-methoxyphenoxy)-1-[4-(1,1-dioxido-3-oxo-2,3-dihydrobenzisothiazol-2-yl)butyl]-pyrrolidine
3-(3-methoxyphenoxy)-1-[5-(1,1-dioxido-3-oxo-2,3-dihydrobenzisothiazol-2-yl)pentyl]-pyrrolidine
3-(3-methoxyphenoxy)-1-[3-(1,1-dioxido-3-oxo-2,3-dihydrobenzisothiazol-2-yl)propyl]-pyrrolidine
3-(3-methoxyphenoxy)-1-[2-(1,1-dioxido-3-oxo-2,3-dihydrobenzisothiazol-2-yl)ethyl]-pyrrolidine
3-(4-methoxyphenoxy)-1-[4-(1,1-dioxido-3-oxo-2,3-dihydrobenzisothiazol-2-yl)butyl]-pyrrolidine
3-(4-methoxyphenoxy)-1-[5-(1,1-dioxido-3-oxo-2,3-dihydrobenzisothiazol-2-yl)pentyl]-pyrrolidine
3-(4-methoxyphenoxy)-1-[3-(1,1-dioxido-3-oxo-2,3-dihydrobenzisothiazol-2-yl)propyl]-pyrrolidine
3-(4-methoxyphenoxy)-1-[2-(1,1-dioxido-3-oxo-2,3-dihydrobenzisothiazol-2-yl)ethyl]-pyrrolidine
3-(1-naphthyloxy)-1-[4-(1,1-dioxido-3-oxo-2,3-dihydrobenzisothiazol-2-yl)butyl]-pyrrolidine
3-(1-naphthyloxy)-1-[5-(1,1-dioxido-3-oxo-2,3-dihydrobenzisothiazol-2-yl)pentyl]-pyrrolidine
3-(1-naphthyloxy)-1-[3-(1,1-dioxido-3-oxo-2,3-dihydrobenzisothiazol-2-yl)propyl]-pyrrolidine
3-(1-naphthyloxy)-1-[2-(1,1-dioxido-3-oxo-2,3-dihydrobenzisothiazol-2-yl)ethyl]-pyrrolidine
3-(2-naphthyloxy)-1-[4-(1,1-dioxido-3-oxo-2,3-dihydrobenzisothiazol-2-yl)butyl]-pyrrolidine
3-(2-naphthyloxy)-1-[5-(1,1-dioxido-3-oxo-2,3-dihydrobenzisothiazol-2-yl)pentyl]-pyrrolidine
3-(2-naphthyloxy)-1-[3-(1,1-dioxido-3-oxo-2,3-dihydrobenzisothiazol-2-yl)propyl]-pyrrolidine
3-(2-naphthyloxy)-1-[2-(1,1-dioxido-3-oxo-2,3-dihydrobenzisothiazol-2-yl)ethyl]-pyrrolidine
3-(2-cyanophenoxy)-1-[4-(1,1-dioxido-3-oxo-2,3-dihydrobenzisothiazol-2-yl)butyl]-pyrrolidine
3-(2-carbamoylphenoxy)-1-[4-(1,1-dioxido-3-oxo-2,3-dihydrobenzisothiazol-2-yl)butyl]-pyrrolidine
3-(2-cyano-6-methoxy-phenoxy)-1-[4-(1,1-dioxido-3-oxo-2,3-dihydro-benzisothiazol-2-yl)butyl]-pyrrolidine
3-[(2-fluorophenyl)-methoxy]-1-[4-(1,1-dioxido-3-oxo-2,3-dihydro-benzisothiazol-2-yl)butyl]-pyrrolidine
3-(2-methoxy-phenoxymethyl)-1-[4-(1,1-dioxido-3-oxo-2,3-dihydro-benzisothiazol-2-yl)butyl]-pyrrolidine
3-(1-naphthylmethoxy)-1-[4-(1,1-dioxido-3-oxo-2,3-dihydrobenzisothiazol-2-yl)butyl]-pyrrolidine
3-(2-naphthylmethoxy)-1-[4-(1,1-dioxido-3-oxo-2,3-dihydrobenzisothiazol-2-yl)butyl]-pyrrolidine
3-(1-carbamoyl-2-naphthyloxy)-1-[4-(1,1-dioxido-3-oxo-2,3-dihydro-benzisothiazol-2-yl)butyl]-pyrrolidine
3-(2-carbamoyl-1-naphthyloxy)-1-[4-(1,1-dioxido-3-oxo-2,3-dihydro-benzisothiazol-2-yl)butyl]-pyrrolidine
3-[4-(1-methyl)indolyl-oxy]-1-[4-(1,1-dioxido-3-oxo-2,3-dihydro-benzisothiazol-2-yl)butyl]-pyrrolidine
3-(2-quinolinyl-oxy)-1-[4-(1,1-dioxido-3-oxo-2,3-dihydrobenzisothiazol-2-yl)butyl]-pyrrolidine
3-(1-isoquinolinyl-oxy)-1-[4-(1,1-dioxido-3-oxo-2,3-dihydro-benzisothiazol-2-yl)butyl]-pyrrolidine
3-(5,6,7,8-tetrahydro-1-naphthyloxy)-1-[4-(1,1-dioxido-3-oxo-2,3-dihydro-benzisothiazol-2-yl)butyl]-pyrrolidine
1-[3-(4-fluorophenyl)sulphonamido-propyl]-3-(2-methoxyphenoxy)-pyrrolidine
1-[2-(4-fluorophenyl)sulphonamido-ethyl]-3-(2-methoxyphenoxy)-pyrrolidine
1-[4-(4-fluorophenyl)sulphonamido-butyl]-3-(2-methoxyphenoxy)-pyrrolidine
1-[3-N-phenyl-(methyl)sulphonamido-propyl]-3-(2-methoxyphenoxy)-pyrrolidine
1-[3-N-methyl-(4-fluorophenyl)sulphonamido-propyl]-3-(2-methoxyphenoxy)-pyrrolidine
1-[4-N-methyl-(4-fluorophenyl)sulphonamido-butyl]-3-(2-methoxyphenoxy)-pyrrolidine
1-[3-(4-fluorophenyl)sulphonamido-propyl]-3-(1-naphthyloxy)-pyrrolidine
1-[2-(4-fluorophenyl)sulphonamido-ethyl]-3-(1-naphthyloxy)-pyrrolidine
1-[4-(4-fluorophenyl)sulphonamido-butyl]-3-(1-naphthyloxy)-pyrrolidine
1-[3-N-methyl-(4-fluorophenyl)sulphonamido-propyl]-3-(1-naphthyloxy)-pyrrolidine
1-[2-N-methyl-(4-fluorophenyl)sulphonamido-ethyl]-3-(1-naphthyloxy)-pyrrolidine
1-[4-N-methyl-(4-fluorophenyl)sulphonamido-butyl]-3-(1-naphthyloxy)-pyrrolidine
1-[3-(1,1-dioxido-2H-naphth[1,8-cd]isothiazol-2-yl)propyl]-3-(2-methoxyphenoxy)-pyrrolidine
1-[2-(1,1-dioxido-2H-naphth[1,8-cd]isothiazol-2-yl)ethyl]-3-(2-methoxyphenoxy)-pyrrolidine
1-[4-(1,1-dioxido-2H-naphth[1,8-cd]isothiazol-2-yl)butyl]-3-(2-methoxyphenoxy)-pyrrolidine
1-(3-aminopropyl)-3-(2-methoxyphenoxy)-pyrrolidine
1-(2-aminoethyl)-3-(2-methoxyphenoxy)-pyrrolidine
1-[3-(1,1-dioxido-2H-naphth[1,8-cd]isothiazol-2-yl)propyl]-(3-(1-naphthyloxy)-pyrrolidine
1-[2-(1,1-dioxido-2H-naphth[1,8-cd]isothiazol-2-yl)ethyl]-3-(1-naphthyloxy)-pyrrolidine
1-[4-(1,1-dioxido-2H-naphth[1,8-cd]isothiazol-2-yl)butyl]-3-(1-naphthyloxy)-pyrrolidine
1-[3-(4,4-dimethyl-2,6-dioxo-piperidin-1-yl)propyl]-3-(2-methoxyphenoxy)-pyrrolidine
1-[2-(4,4-dimethyl-2,6-dioxo-piperidin-1-yl)ethyl]-3-(2-methoxyphenoxy)-pyrrolidine
1-[4-(4,4-dimethyl-2,6-dioxo-piperidin-1-yl)butyl]-3-(2-methoxyphenoxy)-pyrrolidine
1-[3-(1,1-dioxido-3,4-dihydro-4-phenyl-2H-1,2,4-benzothiadiazin-3-on-2-yl)-propyl]-3-(2-methoxyphenoxy)-pyrrolidine
1-[2-(1,1-dioxido-3,4-dihydro-4-phenyl-2H-1,2,4-benzothiadiazin-3-on-2-yl)-ethyl]-3-(2-methoxyphenoxy)-pyrrolidine
1-[4-(1,1-dioxido-3,4-dihydro-4-phenyl-2H-1,2,4-benzothiadiazin-3-on-2-yl)-butyl]-3-(2-methoxyphenoxy)-pyrrolidine
1-(2-cyanoethyl)-3-(2-methoxyphenoxy)-pyrrolidine
1-cyanomethyl-3-(2-methoxyphenoxy)-pyrrolidine
3-(1-naphthyloxy)-1-[4-(2-oxopyrrolidin-1-yl)but-2-in-1-yl]-pyrrolidine
1-[2-(N,N-dimethylsulphamoyl)ethyl]-3-(2-methoxyphenoxy)-pyrrolidine
1-[2-(N,N-diethylsulphamoyl)ethyl]-3-(2-methoxyphenoxy)-pyrrolidine 1-[2-(N-(2-methoxycarbonyl)phenylsulphamoyl)ethyl]-3-(2-methoxyphenoxy)-pyrrolidine
R(−)-3-(2-methoxyphenoxy)-1-[4-(1,1-dioxido-3-oxo-2,3-dihydro-benzisothiazol-2-yl)butyl]-pyrrolidine
S(+)-3-(2-methoxyphenoxy)-1-[4-(1,1-dioxido-3-oxo-2,3-dihydrobenzisothiazol-2-yl)butyl]-pyrrolidine
3-(2-methoxyphenoxy)-1-[4-(1,1-dioxido-2,3-dihydro-benzisothiazol-2-yl)butyl]-pyrrolidine
3-(2-methoxyphenoxy)-1-[2-(3-methylindol-1-yl)-sulphonylethyl]-pyrrolidine
3-(2-methoxyphenoxy)-1-[4-(6(5H)-phenanthridinon-5-yl)butyl]-pyrrolidine
1-[4-(5,5-dioxido-6H-dibenzo[c,e][1,2]thiazin-6-yl)butyl]-3-(2-methoxyphenoxy)-pyrrolidine
1-[3-(1,3-dimethyl-uracil-6-yl)aminopropyl]-3-(2-methoxyphenoxy)-pyrrolidine
1-[2-(prop-2-enyloxy)phenoxy]-1-[4-(1,1-dioxido-3-oxo-2,3-dihydrobenzisothiazol-2-yl)butyl]-pyrrolidine The following are particularly preferred:
3-(2-methoxyphenoxy)-1-[4-(1,1-dioxido-3-oxo-2,3-dihydrobenzisothiazol-2-yl)butyl]-pyrrolidine
3-(3-methoxyphenoxy)-1-[4-(1,1-dioxido-3-oxo-2,3-dihydrobenzisothiazol-2-yl)butyl]-pyrrolidine
3-(1-naphthyl)-1-[4-(1,1-dioxido-3-oxo-2,3-dihydro-benzisothiazol-2-yl)butyl]-pyrrolidine
3-(2-cyano-6-methoxy-phenoxy)-1-[4-(1,1-dioxido-3-oxo-2,3-dihydro-benzisothiazol-2-yl)butyl]-pyrrolidine
1-[2-(4-fluorophenyl)sulphonamido-ethyl]-3-(2-methoxyphenoxy)-pyrrolidine
1-[3-(4-fluorophenyl)sulphonamido-propyl]-3-(2-methoxyphenoxy)-pyrrolidine
1-[4-(1,1-dioxido-2H-naphth[1,8-cd]isothiazol-2-yl)butyl]-3-(2-methoxyphenoxy)-pyrrolidine
1-[4-(1,1-dioxido-2H-naphth[1,8-cd]isothiazol-2-yl)butyl]-3-(1-naphthyloxy)-pyrrolidine
R(−)-3-(2-methoxyphenoxy)-1-[4-(1,1-dioxido-3-oxo-2,3-dihydrobenzisothiazol-2-yl)butyl]pyrrolidine
3-(2-methoxyphenoxy)-1-[4-(2,3-dihydro-benzisothiazol-2yl)butyl]-pyrrolidine Furthermore, a process has been found for the preparation of the 1,3-disubstituted pyrrolidines of the general formula (I) according to the invention

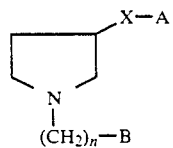

(I)

wherein
A, B, X and n have the abovementioned meanings, which is characterized in that 3-substituted pyrrolidines of the general formula (II)

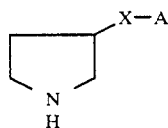

(II)

in which
A and X have the abovementioned meanings, or their salts are reacted in a first step with alkyl derivatives of the general formula (III)

$$R—(CH_2)_n—B'$$ (III)

wherein
n has the abovementioned meaning,
B' corresponds to the range of meaning of B, where, however, $R^5$ and $R^6$ do not stand simultaneously for hydrogen or one for hydrogen and the other for alkyl or aryl,
R stands for chlorine, bromine, iodine, methylsulphonyloxy, phenylsulphonyloxy, tolylsulphonyloxy, trifluoroacetoxy or trifluoromethylsulphonyloxy,
in inert solvents, if appropriate in the presence of bases, then, if desired, functional groups are converted into other functional groups by reduction, oxidation, hydrolysis or reaction with electrophiles or nucleophilic reagents and then, in the case of the preparation of the salts, if desired, the products are reacted with the corresponding acid.

The first step of the process according to the invention (known as method M 1 hereinbelow can be described by way of example by the following reaction equation:

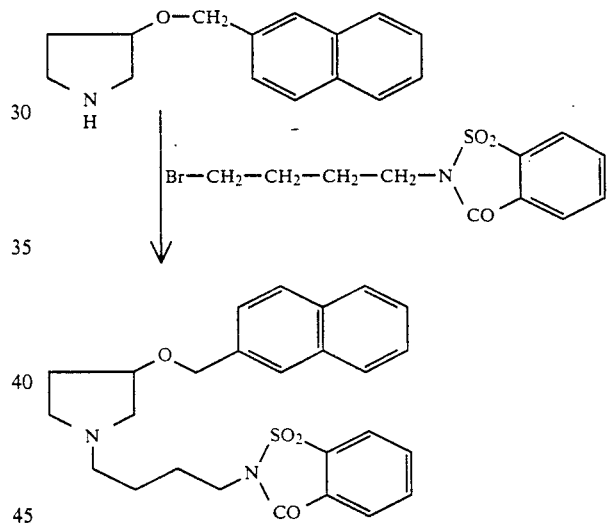

A possible subsequent reaction (identified as method M 2 hereinbelow may be illustrated by way of example by the following reaction equation, in which the nitrile can be prepared according to M 1:

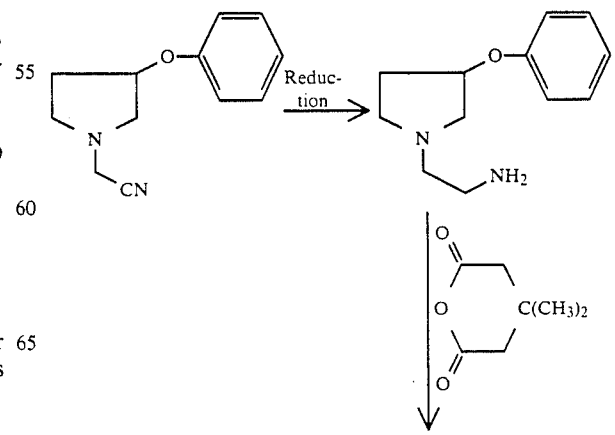

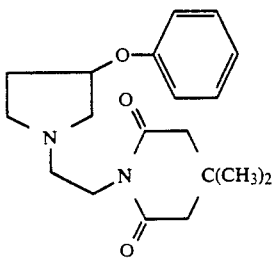

The alkyl compounds of the general formula (III) employed are known or can be prepared by known methods (for example J. March; "Advanced Organic Chemistry", second edition, p. 1170, 1189).

Suitable inert solvents for the process according to method M 1 are the customary organic solvents which are inert under the reaction conditions. These preferably include alcohols such as methanol, ethanol, propanol or isopropanol, or ethers such as diethyl ether, butyl methyl ether, dioxane, tetrahydrofuran, glycol dimethyl ether or diethylene glycol dimethyl ether, or halogenated hydrocarbons such as, for example, methylene chloride, chloroform or carbon tetrachloride, or hydrocarbons such as benzene, toluene, xylene, or petroleum fractions, or amides such as dimethylformamide or hexamethylphosphoric triamide. In addition, it is possible to use mixtures of the solvents mentioned.

The acids formed in the reaction can be bound by the use of excess pyrrolidine (II) or by the use of bases. Alkali metal carbonates and alkaline earth metal carbonates such as sodium carbonate, potassium carbonate, calcium carbonate, hydrogen carbonates such as sodium hydrogen carbonate, metal oxides such as silver oxide, or other inorganic compounds such as silver carbonate can serve as bases. Organic amines can also be employed. Triethylamine, diisopropylamine, 1,8-bis-(dimethylamino)naphthalene may be mentioned by way of example. Triethylamine and potassium carbonate are preferred as bases.

The reaction can be carried out in the absence or in the presence of catalysts. In this connection, alkali metal iodides such as sodium iodide or potassium iodide, which are added to the reaction batch in amounts between 0.5 and 150 mole percent, preferably 5 to 50 mole per cent, are particularly suitable.

The reaction is in general carried out in a temperature range from $-20°$ C. to $+150°$ C., preferably from $+20°$ C. to $+100°$ C. The reaction can be carried out at atmospheric, elevated or reduced pressure. In general, the reaction is carried out at atmospheric pressure.

When carrying out the reaction, the starting materials are in general employed in a molar ratio of pyrrolidine (II) to alkyl compound (III) of 0.5:1 to 1.1:1. The base added to bind the reaction product HR is in this case employed in an equimolar amount or in an up to 20-fold excess. The reaction is preferably carried out using a ratio of pyrrolidine:alkyl compound:base of 1:1:1 to 1:1:4. If the reaction is carried out without base, the molar ratio of pyrrolidine (II) to alkyl compound (III) is 1:1 to 5:1. The reaction is preferably carried out using a molar ratio of 2:1.

The conversion of functional groups into other functional groups by method M 2 is carried out, depending on the functional groups, by oxidation, reduction, hydrolysis or by reaction with electrophilic or nucleophilic reagents and is illustrated as follows:

M 2.1

The reduction of the nitrile group to the amino group is in general carried out using metal hydrides, preferably using lithium aluminum hydride, aluminum hydride (prepared, for example, by reaction of lithium aluminum hydride with 100% strength sulphuric acid or with aluminum chloride) or their mixtures in inert solvents such as ethers or chlorinated hydrocarbons, preferably in ethers such as, for example, tetrahydrofuran, diethyl ether or dioxane in a temperature range from $-20°$ C. to $+100°$ C., preferably from $0°$ C. to $+50°$ C. at atmospheric pressure.

Reduction is additionally possible by hydrogenating the nitriles in inert solvents such as alcohols, for example methanol, ethanol, propanol or isopropanol in the presence of a noble metal catalyst such as platinum, palladium, palladium on animal charcoal or Raney nickel, in a temperature range from $0°$ C. to $+150°$ C., preferably from room temperature to $+100°$ C. at atmospheric pressure or at overpressure.

The reaction can be illustrated by the following equation:

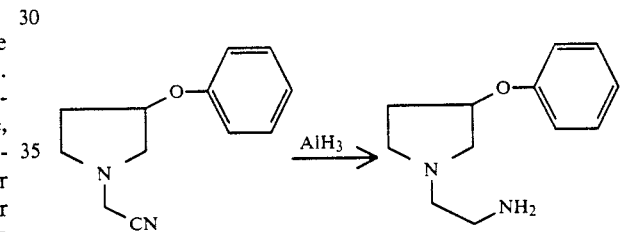

M 2.2

The reaction of compounds with $R^5$=meaning as above, $R^6$=H, with acylating agents such as acid chlorides is in general carried out in inert solvents such as ethers, hydrocarbons or halogenated hydrocarbons or their mixtures, preferably in ethers such as, for example, diethyl ether, tetrahydrofuran, or halogenated hydrocarbons such as methylene chloride or chloroform, if appropriate in the presence of bases such as alkali metal carbonates, for example, sodium carbonate or potassium carbonate, or organic amines such as, for example, triethylamine or pyridine, in a temperature range from $-20°$ C. to $+100°$ C., preferably from $0°$ C. to $+60°$ C. at atmospheric pressure.

The reaction can be illustrated by the following equation:

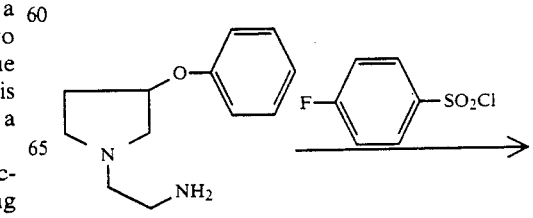

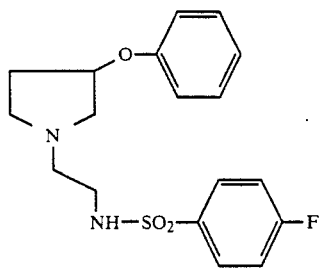

If the reaction is carried out without organic or inorganic bases, the compounds according to the invention are obtained in the form of their salts, from which the free base is available, for example by treating with bicarbonate.

M 2.3

Cyclic imides of the general formula (I) are in general prepared by the reaction of amino compounds of the type I ($R^5=H$, $R^6=H$) with cyclic anhydrides in inert solvents such as ethers, hydrocarbons or halogenated hydrocarbons or their mixtures, preferably in hydrocarbons such as benzene, toluene, xylene, if appropriate in the presence of organic bases, preferably triethylamine or tributylamine, if appropriate with removal of the water of reaction, preferably by azeotropic distillation or by the addition of activated molecular sieve, in a temperature range from $+20°$ C. to $+150°$ C., preferably $+20°$ C. to the boiling point of the solvent. Working without solvent at elevated temperature is likewise possible.

The process may be illustrated by the following example:

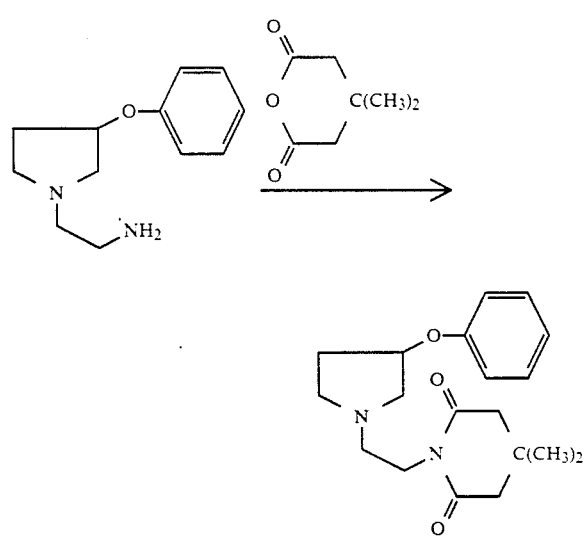

Compounds in which n is equal to 2 and B stands for cyano or a group of the formula $-SO_2NR^2R^3$ or $-SO_mR^4$, where $R^2$, $R^3$, $R^4$ and m have the abovementioned meanings, can be prepared by a particular process variant (identified as method M 3 hereinbelow).

A process has now been found for the preparation of 1,3-disubstituted pyrrolidines of the general formula (I)

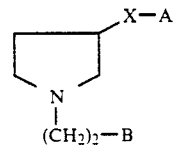

wherein
A and X have the abovementioned meaning, and
B stands for cyano or a group of the formula $-SO_2NR^2R^3$ or $-SO_mR^4$, wherein $R^2$, $R^3$, $R^4$ and m have the abovementioned meanings, characterized in that 3-substituted pyrrolidines of the general formula (II)

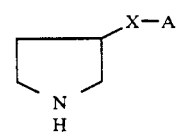

wherein
A and X have the abovementioned meanings, or their salts, are reacted with acrylonitrile or with a group of the formula $CH_2=CH-SO_2NR^2R^3$ or $CH_2=CH-SO_mR^4$, wherein $R^2$, $R^3$, $R^4$ and m have the abovementioned meanings, in the presence of catalysts (method M 3).

Of course, it is possible to prepare, according to method M 2, further pyrrolidines according to the invention from the nitriles.

The following reaction equation illustrates this process (method M 3):

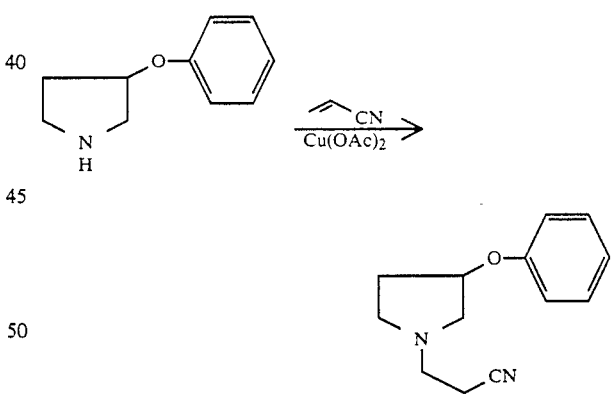

Salts of the pyrrolidines of the formula II for the process according to the invention are, for example, hydrohalides (such as hydrochlorides) or trifluoroacetates.

Catalysts for the process variant according to the invention are, for example, copper salts, preferably copper(II) acetate.

The variant is in general carried out in a temperature range from $+50°$ C. to $+150°$ C., preferably from $+90°$ C. to $+110°$ C., at atmospheric, elevated or reduced pressure, preferably at atmospheric pressure.

The pyrrolidines of the formula II and the olefin are in general employed in the ratio 0.5 to 20, preferably 1 to 5, mole equivalents.

The amount of copper salt employed is 0.5 to 10, preferably 1 to 5, mole %, relative to the pyrrolidine of the formula II.

If salts of the pyrrolidines II are used, 1 to 10, preferably 1 to 3, mole equivalents of base, relative to II, can be employed. Inorganic and organic bases, preferably triethylamine, are used as bases.

The process variant can, of course, be carried out in inert solvents.

The 3-substituted pyrrolidines of type II used for the preparation of the compounds (I) according to the invention according to methods M 1 to M 3 are either known [J. Med. Chem. 12, 435 to 441 (1969)] or can be prepared according to method P from pyrrolidines of the formula IV

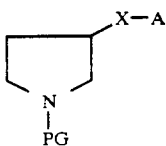

wherein

A and X have the abovementioned meanings, and PG stands for a nitrogen-protecting group which can be eliminated by customary methods of organic chemistry (Th. Greene, "Protective Groups in Organic Synthesis", 1st edition, J. Wiley and Sons, New York, 1981). The protecting groups can be eliminated, for example, by hydrolysis or hydrogenolysis.

For the case in which the radical X-A stands for O-aryl, the pyrrolidines (IV) are producible from the corresponding hydroxypyrrolidines and the corresponding hydroxyaromatics in a manner known per se. If X-A stands for —O—CH$_2$-aryl, these compounds can be obtained from the corresponding aryl-methyl halides and the corresponding hydroxypyrrolidines in a manner known per se.

3-Hydroxymethyl-pyrrolidines yield pyrrolidines of the formula (IV), in which X-A stands for —CH$_2$—O-aryl, by reaction with the corresponding hydroxyaromatics in a manner known per se.

The invention includes both enantiomers of the pyrrolidines of the type I (=Ia, Ib)

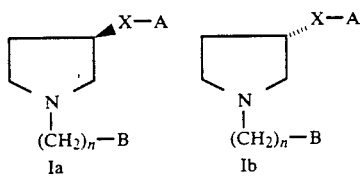

wherein

A, B, X and n have the abovementioned meanings, and their mixtures.

The mixtures deviating from the ratio Ia/Ib=1:1 and the pure isomers are expediently obtained by the use of customary methods for the synthesis of optically active compounds.

Examples which may be mentioned are the formation and resolution of diastereomeric salts (with optically active acids) of the compounds I, II, IV, (inasmuch as PG is not acyl or alkoxycarbonyl), with subsequent release of the base and the use of optically active starting materials [D. Flanagan +M. Joullie, Heterocycles 26, 2247 (1987)].

The pyrrolidines according to the invention have a superior pharmacological action, in particular on the central nervous system, and can be employed as active compounds in medicaments.

In particular, the pyrrolidines according to the invention have a high affinity for cerebral 5-hydroxytryptamine receptors of the 5-HT$_1$ type. Connected with this are agonistic, partially agonistic or antagonistic actions on the serotonin receptor.

The high affinity ligands for the serotonin-1 receptor described in the present invention thus represent active compounds for combating diseases which are distinguished by disturbances of the serotoninergic system, in particular with the involvement of receptors which have a high affinity for 5-hydroxytryptamine (5-HT$_1$ type). They are therefore suitable for the treatment of diseases of the central nervous system such as anxiety, tension and depressive states, sexual ·dysfunctions caused by the central nervous system and disturbances of sleep and nutritional absorption. Furthermore, they are suitable for the elimination of cognitive deficits, for the improvement of powers of learning and memory and for the treatment of Alzheimer's disease. Furthermore, these active compounds are also suitable for the modulation of the cardiovascular system. They also intervene in the regulation of the cerebral circulation and thus represent powerful agents for combating migraine. They are also suitable as prophylactics and for combating the consequences of the occurrence of cerebral infarcts (Apoplexia cerebri) such as strokes and cerebral ischaemia. The compounds according to the invention can also be used for combating pain states. They can also be used for combating diseases of the intestinal tract which are distinguished by disturbances of the serotoninergic system, and disturbances of the carbohydrate metabolism.

The new active compounds can be converted in a known manner into the customary formulations, such as tablets, dragees, pills, granules, aerosols, syrups, emulsions, suspensions and solutions, using inert, non-toxic, pharmaceutically suitable excipients or solvents. In these formulations, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, if necessary organic solvents can be used as auxiliary solvents.

Examples of auxiliaries which may be mentioned are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, argillaceous earths, talc, chalk), ground synthetic minerals (for example highly disperse silica, silicates), sugars (for example sucrose, lactose and dextrose), emulsifiers (for example polyoxyethylene fatty acid acid esters), polyoxyethylene fatty alcohol ethers (for example ligninsulphite waste liquors, methylcellulose, starch and polyvinylpyrrolidone) and lubricants (for example magnesium stearate, talc, stearic acid and sodium lauryl sulphate).

Administration is carried out in a customary manner, preferably orally or parenterally, in particular perlingually or intravenously. In the case of oral administration, tablets can, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can be additionally used for tableting. In the case of aqueous suspensions, various flavor-improvers or colourants can be added to the active compounds in addition to the abovementioned auxiliaries.

In the case of parenteral administration, solutions of the active compounds can be employed using suitable liquid excipients.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this, it may be necessary to deviate from the amounts mentioned, depending on the body weight or the type of administration route, on individual behavior towards the medicament, the nature of its formulation and the point in time or interval at which administration is carried out. Thus, in some cases it may be sufficient to manage with less than the previously mentioned minimum amount, whereas in other cases the upper limit mentioned must be exceeded. In the case of the administration of larger amounts, it may be advisable to divide these into a number of individual doses over the day.

Preparation Examples

The $R_f$ values mentioned in each case were determined—unless stated otherwise—by thin layer chromatography on silica gel (aluminum foil, silica gel 60 F 254, E. Merck). The visualization of the substance spots took place by examination under UV light and/or by spraying with 1% strength potassium permanganate solution.

Flash chromatography was carried out on silica gel 60, 0.040–0.064 mm, E. Merck (see Still et al., J. Org. Chem. 43, 2923, 1978; for simpler separation problems see Aldrichimica Acta 18, 25, 1985). Elution with solvent gradients means: beginning with the pure, non-polar solvent mixture component, the polar solvent component is admixed to an increasing extent, until the desired product is eluted (checked by TLC).

In all products, the solvent was finally distilled off at about 0.1 Torr. Salts were stored at this pressure overnight over potassium hydroxide and/or phosphorus pentoxide.

EXAMPLE 1 (METHOD M 1)

3-(2-Cyanophenoxy)-1-[4-(1,1-dioxido-3-oxo-2,3-dihydrobenzisothiazol-2-yl)butyl]-pyrrolidine oxalate

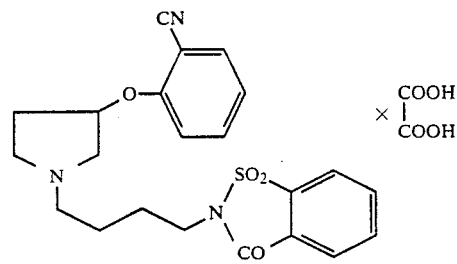

1.88 g (10 mmol) of 3-(2-cyanophenoxy)-pyrrolidine, 3.18 g (10 mmol) of 2-(4-bromobutyl)-benzisothiazol-3(2H)-one 1,1-dioxide and 1.01 g (10 mmol) of triethylamine were dissolved in 40 ml of dry dimethylformamide and the mixture was stirred for 20 hours at 45° C. with the exclusion of moisture. The solvent was removed in a high vacuum and the remaining residue was purified by flash chromatography (toluene-ethyl acetate and toluene-ethanol gradients). The product (2.90 g) was obtained as a yellow oil.

The $^1$H-NMR spectrum indicated the presence of about 10% of dimethylformamide in this product.

$^1$H-NMR (CDCl$_3$): δ=1.65 (quintet, 2H); 1.95 (quintet, 2H); 2.1 (m, 1H); 2.35 (m, 1H); 2.6–3.0 (m, also contains signals from dimethylformamide); 3.3 (dd, 1H); 3.8 (t, 2H); 4.95 (m, 1H); 6.9 (d, 1H); 7.0 (dd, 1H); 7.5 (m, 2H); 7.8–8.1 (m, contains signals from dimethylformamide). Yield: 61%. $R_f$=0.48 (toluene/methanol 4:1; silica gel plates).

The oxalate was obtained from this by treating with anhydrous oxalic acid in warm, anhydrous ethanol. Recrystallization from acetone/ethyl acetate/tert.butyl methyl ether gave colorless crystals (1.68 g) of melting point 135°–139° C.

This method was employed in a similar manner to obtain the compounds I of Table 1 (method M 1). If pyrrolidines of the type II were used in the form of their hydrochlorides, a 2- to 3-fold amount of triethylamine was used.

EXAMPLE 2 (METHOD M 2.1)

1-(3-Aminopropyl)-3-(2-methoxyphenoxy)-pyrrolidine 1,5-naphthalenedisulphonate

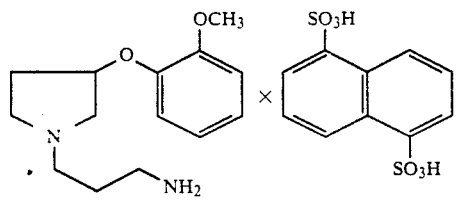

2.06 g of a mixture of 95% strength sulphuric acid and 20% strength oleum in the ratio 1:1 was cautiously added to a suspension of 1.6 g (42 mmol) of lithium aluminum hydride in 50 ml of ether at 0° C. After 1 h at room temperature, 3.5 g (14 mmol) of 1-(2-cyanoethyl)-3-(2-methoxyphenoxy)-pyrrolidine in 70 ml of ether were added dropwise. The mixture was heated to reflux for 2 h. 9.3 ml of water and 18.6 ml of 10% strength sodium hydroxide solution were added with ice cooling. Stirring with kieselguhr, filtering off with suction over kieselguhr, subsequently washing the filter cake with ethyl acetate, drying and evaporating gave 3.4 g of the free base as a yellow oil (96%).

MS (FAB): 251 (M+1).

¹H-NMR (CDCl₃): δ=1.2–1.5 (broad signal, about 2H; —NH₂); 1.65 (quintet, 2H); 2.05 (m, 1H); 2.25 (m, 1H); 2.5–2.8 (m, 7H); 3.0 (dd, 1H); 3.75 (s, 3H); 4.85 (m, 1H); 6.75–6.95 (m, 4H).

R_f=0.1 (toluene/methanol 4:1; silica gel plates).

The salt (1:1 adduct) was obtained from 1.2 g of this product with 1,5-naphthalenedisulphonic acid in hot ethanol in the form of beige crystals (1.7 g).

Melting point: from 187° C. with foaming.

EXAMPLE 3 (METHOD M 2.2)

1-[3-(4-Fluorophenyl)sulphonamido-propyl]-3-(2-methoxyphenoxy)-pyrrolidine hydrochloride

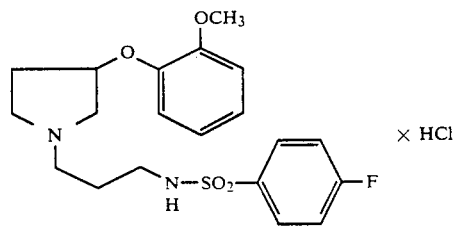

0.78 g (4.0 mmol) of 4-fluorophenylsulphonyl chloride in 15 ml of ether were added dropwise to a solution of 1.0 g (4.0 mmol) of 1-(3-aminopropyl)-3-(2-methoxyphenoxy)-pyrrolidine in 20 ml of anhydrous ether at 0° C. After 2 hours at room temperature, the mixture was freed from solvent in vacuo and the remaining oily residue was brought to crystallization by trituration with diethyl ether/hexane. In this manner, 1.1 g (62%) of title compound were obtained as a slightly reddish, hygroscopic solid. It melted from 50° C.

MS (FAB): 409 (M+1)

R_f=0.2 (toluene/methanol 4:1, silica gel plates) [free base]

EXAMPLE 4 (METHOD M 2.3)

1-[3-(4,4-Dimethyl-2,6-dioxo-piperidin-1-yl)-propyl]-3-(2-methoxyphenoxy)-pyrrolidine (salt with 1,5-naphthalenedisulphonic acid)

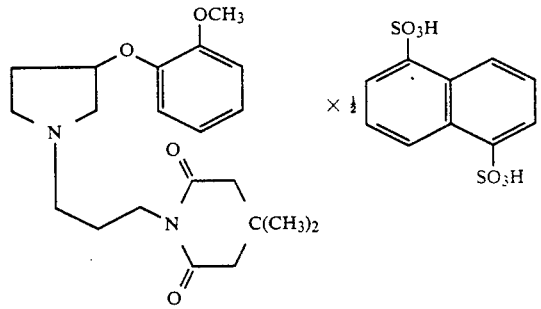

A solution of 1.0 g (4.0 mmol) of 1-(3-aminopropyl)-3-(2-methoxyphenoxy)-pyrrolidine, 0.57 g (4.0 mmol) of 3,3-dimethylglutaric anhydride and 4 drops of tributylamine were heated to reflux in the presence of 2 g of molecular sieve (3 Å). After 2 hours, the mixture was filtered and freed from solvent in vacuo. The residue obtained in this way was purified by flash chromatography (toluene/ethyl acetate and ethyl acetate-ethanol gradient).

1.0 g (67%) of free base was obtained as a yellow oil.

R_f=0.6 (toluene/methanol 4:1, silica gel plates)

IR (CHCl₃): 3008, 2965, 2814, 1727, 1672, 1593, 1503.

The salt (as the 2:1 compound) was precipitated from this in hot ethanol using 1,5-naphthalenedisulphonic acid.

Melting point: 195°–200° C. (colorless crystals)

EXAMPLE 5 (METHOD M 3)

1-(2-Cyanoethyl)-3-(2-methoxyphenoxy)pyrrolidine (as the salt of 1,5-naphthalenedisulphonic acid)

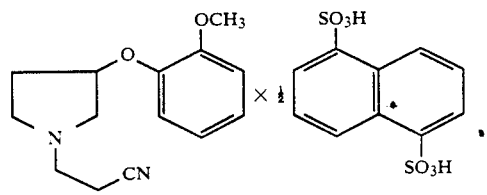

0.1 g of copper (II) acetate was added to 5.0 g (22 mmol) of 3-(2-methoxyphenoxy)-pyrrolidine hydrochloride, 2.43 g (24 mmol) of triethylamine and 5.8 g (109 mmol) of acrylonitrile and the mixture was stirred for 4 hours at 110° C. The reaction batch was purified by flash chromatography (silica gel, toluene/ethyl acetate gradient). 5.0 g (93%) of the free base were obtained as a yellowish oil.

MS (m/z): 246, 206, 123, 83, 82

R_f=0.3 (toluene/methanol 4:1, silica gel plates)

IR (CHCl₃): 3030, 3003, 2951, 2822, 2254, 1593, 1503.

Treating the free base with 1,5-naphthalenedisulphonic acid in hot ethanol gave the 2:1 salt of the title compound as a colorless solid.

Melting range: 85°–95° C.

EXAMPLES 6 TO 45

The examples are summarized in Table 1:

| Legend to Table 1: | |
|---|---|
| (a) | Abbreviations used in column B: |
| SACCH = | 1,1-dioxido-2,3-dihydro-3-oxo-benzisothiazol-2-yl |
| FSULF = | [(4-fluorophenyl)sulphonyl]amino |
| NPSULF = | [N-phenyl-N-methylsulphonyl]amino |
| TDIAZ = | 1,1-Dioxido-3-oxo-4-phenyl-3,4-dihydro-2H-1,2,4-benzothiadiazin-2-yl |
| NAPHT = | 1,1-dioxido-2H-naphth[1,8-cd]isothiazol-2-yl |
| DMP = | 4,4-dimethyl-2,6-dioxo-piperidin-2-yl |
| NH₂ = | amino |
| CN = | cyano |
| PYRR = | 3-(2-oxopyrrolidin-1-yl)prop-1-inyl |
| DES = | N,N-diethylsulphamoyl |
| DMS = | N,N-dimethylsulphamoyl |
| BITZ = | 1,1-Dioxido-2,3-dihydro-benzthiazol-2-yl |
| SANTH = | N-(2-methoxycarbonylphenyl)sulphamoyl |
| SIND = | 3-methyl-indol-1-yl-sulphonyl |
| PHEN = | 6(5H)-phenanthridinon-5-yl |
| DBTH = | 5,5-dioxido-6H-dibenzo[c,e][1,2]thiazin-6-yl |
| DMUR = | (1,3-dimethyl-uracil-6-yl)amino |
| (b) | Abbreviations used for the eluents |
| KTM = | toluene/methanol 4:1; silica gel plates |
| KDM = | dichloromethane/methanol 10:1; silica gel plates |
| ADM = | dichloromethane/methanol 100:1; alumina plates |
| AE = | ethanol; alumina plates |
| KTE = | toluene/ethyl acetate 1:1, silica gel plates |
| (c) | Abbreviations used for the salts |
| OX = | salt of oxalic acid |
| NS = | salt of 1,5-naphthalenedisulphonic acid (stoichiometry = 2 moles of base/1 mole of acid) |
| NDS = | salt of 1,5-naphthalenedisulphonic acid |

| | Legend to Table 1: | | | Legend to Table 1: |
|---|---|---|---|---|
| Cl = | salt of hydrochloric acid | | R = | 5-(4-bromobutyl)-6(5H)-phenanthridinone |
| | (1 mole of base/1 mole of acid) | | S = | 6-(4-bromobutyl)-6H-dibenzo[c,e][1,2]-thiazine 5,5-dioxide |
| W = | salt of L-tartaric acid | | T = | 6-(3-chloropropyl)amino-1,3-dimethyluracil |
| F = | free base | | (e) | $^1$H-NMR (CD$_3$OD): δ = 1.8–2.0 (m, 4H); 2.1– |
| (d) | Abbreviations used for the educts | | | 2.4 (m, 1H); 2.5–2.8 (m, 1H); 3.2–3.5 (m, contains |
| A = | 2-(4-bromobutyl)-2H-benzisothiazol-3-one 1,1-dioxide | | | signals from the solvent); 3.7–4.2 (m, 4H); 5.2 (m, 1H); 6.85–7.0 (m, 3H); 7.2–7.4 (m, 2H); 7.75–8.15 |
| B = | chloroacetonitrile | | | (m, 4H). |
| C = | acrylonitrile | | (f) | R(−)-enantiomer from Example 8; α$_D^{20}$ = −7.0 |
| D = | 2-(4-bromobutyl)-2H-naphth[1.8-cd]isothiazole 1,1-dioxide | | | (c = 1, CH$_3$OH) |
| | | | (g) | syrupy, solidifies after digeration with diethylether, |
| E = | 2-(4-bromobutyl)-3,4-dihydro-4-phenyl-2H-1,2,4-benzothiadiazin-3-one 1,1-dioxide | | (h) | $^1$H-NMR (CD$_3$OD): δ = 1.05 (s, 6H); 2.1–2.7 (m, 6H); 3.3–3.6 (m, contains signals from the |
| F = | (4-fluorophenyl)sulphonyl chloride | | | solvent); 3.7–4.2 (m, among them: 3.75, s, OCH$_3$; |
| G = | 3.3-dimethylglutaric anhydride | | | 7H); 5.1 (m, 1H); 6.85–7.1 (m, 4H). |
| H = | aluminum hydride | | (i) | elemental analysis C$_{23}$H$_{28}$N$_2$O$_5$S × C$_4$H$_6$O$_6$ |
| I = | N-(4-bromobutyl)-N-phenyl-methanesulphonamide | | (k) | $^{13}$C-NMR (CDCl$_3$) 25.4 (t). 26.5 (t). 32.1 (t). 36.9 |
| K = | 2-(3-brompropyl)-2H-benzisothiazol-3-one 1,1-dioxide | | | (q). 50.4 (t). 52.8 (t). 55.6 (t). 55.9 (q). 60.3 (t). 77.6 |
| L = | N,N-dimethyl-vinylsulphonamide | | | (d). 112.1 (d). 114.8 (d). 120.8 |
| M = | N,N-diethyl-vinylsulphonamide | | | (d). 121.3 (d). 128.0 (d). 128.5 |
| N = | 2-(4-bromobutyl)-2,3-dihydrobenzisothiazole-1,1-dioxide | | | (d). 129.5 (d). 139.1 (s). 147.4 (s). 150.0 (s). |
| O = | methyl 2-(ethenesulphonylamino)benzoate [from methyl anthranilate and 2-chloroethanesulphonyl chloride in the presence of excess triethylamine] | | (l) | from Example 57 by reaction with 1-(prop-2-inyl)-2-pyrrolidone and paraformaldehyde in the presence of copper(II) acetate |
| P = | 3-methyl-1-vinylsulphonyl-indole [from 3-methyl-indole and 2-chloroethanesulphonyl chloride in the presence of excess triethylamine] | | (m) | S(+)-enantiomer from Example 8 α$_D^{20}$ = +7.1 (c = 1, CH$_3$OH) |

TABLE 1

Compounds of the general formula (I)

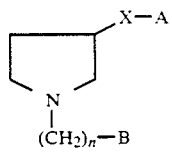

| Ex. | —X—(A) | —A | —B$^{(a)}$ | n | R$_f$/Solvent$^{(b)}$ | Salt$^{(c)}$/Melting point (°C.) | prepared from$^{(d)}$ | Method |
|---|---|---|---|---|---|---|---|---|
| 6 | —O— | Phenyl | SACCH | 4 | 0.35 (KTM) | Cl; amorphous$^{(e)}$ | Ex. 48 + A | M 1 |
| 7 | —OCH$_2$— | Phenyl | SACCH | 4 | 0.4 (KDM) | NS; 155–158 | Ex. 49 + A | M 1 |
| 8 | —O— | 2-Methoxyphenyl | SACCH | 4 | 0.35 (KTM) | OX; 134 | Ex. 50 + A | M 1 |
| 9$^{(f)}$ | —O— | 3-Methoxyphenyl | SACCH | 4 | 0.52 (KDM) | F; $^{(g)}$ | Ex. 55 + A | M 1 |
| 10 | —O— | 3-Methoxyphenyl | SACCH | 4 | 0.52 (KDM) | NS; 173–178 | Ex. 51 + A | M 1 |
| 11 | —O— | 2-Methoxyphenyl | NH$_2$ | 2 | 0.1 (KTM) | NDS; >220 | Ex. 14 + H | M 2.1. |
| 12 | —O— | 2-Methoxyphenyl | FSULF | 2 | 0.4 (KTM) | Cl; 98–110 | Ex. 11 + F | M 2.2. |
| 13 | —O— | 2-Methoxyphenyl | DMP | 2 | 0.3 (KTM) | Cl; hygr.$^{(h)}$ | Ex. 11 + G | M 2.3. |
| 14 | —O— | 2-Methoxyphenyl | CN | 1 | 0.57 (KTM) | F; 73–76 | Ex. 50 + B | M 1 |
| 15 | —CH$_2$O— | 2-Methoxyphenyl | SACCH | 4 | 0.34 (ADM) | W; amorphous$^{(i)}$ | Ex. 46 + A | M 1 |
| 16 | —O— | 2-Methoxyphenyl | NPSULF | 4 | 0.24 (KTM) | F;$^{(k)}$ | Ex. 50 + I | M 1 |
| 17 | —O— | 2-Methoxyphenyl | NAPHT | 4 | 0.35 (KTM) | NS; 115–117 | Ex. 50 + D | M 1 |
| 18 | —O— | 2-Methoxyphenyl | TDIAZ | 4 | 0.38 (KDM) | Cl; amorphous | Ex. 50 + E | M 1 |
| 19 | —O— | (2-Carbamoyl)-phenyl | SACCH | 4 | 0.75 (AE) | NDS; >220 | Ex. 53 + A | M 1 |
| 20 | —O— | (2-Methoxy-6-cyano)phenyl | SACCH | 4 | 0.38 (KTM) | NS; 165(dec.) | Ex. 47 + A | M 1 |
| 21 | —O— | (1-Cyano)-naphth-2-yl | SACCH | 4 | 0.59 (KDM) | F; 132–134 | Ex. 54 + A | M 1 |
| 22 | —O— | (2-Carbamoyl)-naphth-1-yl | SACCH | 4 | 0.44 (KDM) | NS; >167 (sintering) | Ex. 56 + A | M 1 |
| 23 | —O— | Naphth-1-yl | SACCH | 4 | 0.50 (KDM) | NS; 209–215 | Ex. 57 + A | M 1 |
| 24 | —O— | Naphth-2-yl | SACCH | 4 | 0.53 (KDM) | OX; 142–149 | Ex. 58 + A | M 1 |
| 25 | —OCH$_2$— | Naphth-1-yl | SACCH | 4 | 0.35 (KDM) | OX; amorphous | Ex. 59 + A | M 1 |
| 26 | —OCH$_2$— | Naphth-2-yl | SACCH | 4 | 0.4 (KDM) | NS; 138 | Ex. 60 + A | M 1 |
| 27 | —OCH$_2$— | 2-Fluorphenyl | SACCH | 4 | 0.23 (KDM) | NS; 143–148 | Ex. 61 + A | M 1 |
| 28 | —O— | (1-Methyl)indol-4-yl | SACCH | 4 | 0.44 (KDM) | NS; >162(dec.) | Ex. 62 + A | M 1 |
| 29 | —O— | Naphth-1-yl | NAPHT | 4 | 0.64 (KDM) | Cl; 192–193 | Ex. 57 + D | M 1 |
| 30 | —O— | 4-Methoxyphenyl | SACCH | 4 | 0.6 (KDM) | NS; 192–196 | Ex. 63 + A | M 1 |
| 31 | —O— | 5,6,7,8-Tetra-hydro-naphth-1-yl | SACCH | 4 | 0.38 (KDM) | NS; 190–192 | Ex. 64 + A | M 1 |
| 32 | —O— | Quinolin-2-yl | SACCH | 4 | 0.28 (KTM) | NDS; 200(dec.) | Ex. 65 + A | M 1 |
| 33 | —O— | Isoquinolin-1-yl | SACCH | 4 | 0.63 (KDM) | NDS; 180(dec.) | Ex. 66 + A | M 1 |
| 34 | —O— | Naphth-1-yl | PYRR | 1 | 0.75 (KDM) | Cl; 138–140 | | l) |
| 35 | —O— | 2-Methoxyphenyl | SACCH | 3 | 0.44 (KTM) | NS; ab 225 | Ex. 50 + K | M 1 |

TABLE 1-continued

Compounds of the general formula (I)

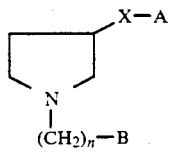

| Ex. | —X—(A) | —A | —B(a) | n | Rf/Solvent(b) | Salt(c)/Melting point (°C.) (dec.) | prepared from(d) | Method |
|---|---|---|---|---|---|---|---|---|
| 36 | —O— | 2-Methoxyphenyl | DMS | 2 | 0.24 (KTM) | NS; 162–164 | Ex. 50 + L | M 3 |
| 37 | —O— | 2-Methoxyphenyl | DES | 2 | 0.30 (KTM) | NS; 145–150 | Ex. 50 + M | M 3 |
| 38(m) | —O— | 2-Methoxyphenyl | SACCH | 4 | 0.50 (KDM) | F; 70–73 | Ex. 67 + A | M 1 |
| 39 | —O— | 2-Methoxyphenyl | BITZ | 4 | 0.44 (KDM) | NS; 150–156 | Ex. 50 + N | M 1 |
| 40 | —O— | 2-Methoxyphenyl | SANTH | 2 | 0.36 (KTE) | NS; 168–170 | Ex. 50 + O | M 3 |
| 41 | —O— | 2-Methoxyphenyl | SIND | 2 | 0.46 (KTE) | F; 156–158 | Ex. 50 + P | M 3 |
| 42 | —O— | 2-Methoxyphenyl | PHEN | 4 | 0.31 (KDM) | Cl; 169–170 | Ex. 50 + R | M 1 |
| 43 | —O— | 2-Methoxyphenyl | DBTH | 4 | 0.48 (KDM) | NS; 182–186 | Ex. 50 + S | M 1 |
| 44 | —O— | 2-(Prop-2-enyl-oxy)phenyl | SACCH | 4 | 0.46 (KDM) | NS; 138–142 | Ex. 68 + A | M 1 |
| 45 | —O— | 2-Methoxyphenyl | DMUR | 3 | 0.35 (KDM) | NDS; 199(dec.) | Ex. 50 + T | M 1 |

STARTING COMPOUNDS

EXAMPLE 46

3-(2-Methoxyphenoxy)methyl-pyrrolidine

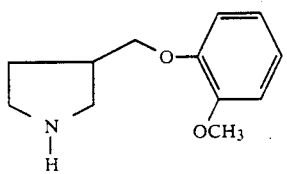

5.0 g of 10% palladium on activated carbon were added to a solution of 5.0 g (17 mmol) of 1-benzyl-3-(2-methoxyphenoxy)methyl-pyrrolidine and 10.6 g (0.17 mol) of ammonium formate in 300 ml of methanol and the mixture was heated to reflux for 1 hour. After cooling, the solution was separated from the catalyst by filtration and the filtrate was freed from solvent in vacuo. The residue was rendered basic using 1N NaOH and the mixture was extracted using ether. After drying and evaporating, 1.5 g (43%) of the title compound were obtained as an oil.

$R_f$=0.35 (dichloromethane/methanol 20:1; alumina plates) (cf. DE-A 2,315,092)

EXAMPLE 47

3-(2-Cyano-6-methoxy)phenoxy-pyrrolidine hydrochloride

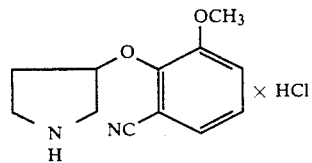

14.8 ml (59.4 mmol) of 4M hydrogen chloride in anhydrous dioxane were added at 0° C. to 6.3 g (19.8 mmol) of 1-tert.butoxycarbonyl-3-(2-cyano-6-methoxy-phenoxy)-pyrrolidine. After 2 hours at room temperature, 7.4 ml of 4M hydrogen chloride in dioxane were again added. After a further 2 hours, the mixture was concentrated. The residue was triturated with toluene and allowed to crystallize overnight under toluene. In this manner, 4.2 (83%) of light reddish crystals were obtained.

Melting point: 132° C. (from 98° C.: sintering)
$R_f$=0.14 (dichloromethane/methanol 10:1, silica plates) [free base]

EXAMPLES 48 TO 68

Examples 48 to 68 are summarized in Table 2; they are obtained analogously to Example 46 and 47.

| Legend to Table 2 |
|---|
| (a) TLC system: silica gel plates<br>Eluent:<br>TET = toluene/ethanol/triethylamine 5:3:1<br>DM = dichloromethane/methanol 10:1 |
| (b) salts:<br>Cl = hydrochloride; F = free base |
| (c) preparation from Ex. 72 using trifluoroacetic acid at 0° C./45 minutes and subsequent release of the base with alkali.<br>$^1$H-NMR (CDCl$_3$): δ = 2.0–2.3 (m, about 4H, also contains signal from —NH and traces of water); 2.9–3.3 (m, 4H); 4.9 (m, 1H); 6.85–7.1 (m, 2H); 7.45–7.6 (m, 2H). |
| (d) sintering from 98° C. |
| (e) from Ex. 52 |
| (f) reacted further as a crude product to give Example 9 |
| (g) amorphous, hygroscopic solid<br>$^1$H-NMR (CD$_3$OD): δ = 2.0–2.5 (m, 2H); 3.4–3.8 (m, 4H); 5.15 (m, 1H); 7.5–8.3 (m, 6H). |
| (h) dihydrochloride; directly reacted further to give Example 28. |
| (i) 3 equivalents of HCl in dioxane employed; dihydrochloride, amorphous, hygroscopic<br>$^1$H-NMR (CD$_3$OD): δ = 2.5 (mc, 2H); 3.55 (mc, 2H); 3.75 (mc, 2H); 5.9 (m, 1H); 7.4 (d, 1H); 7.6 (m, 1H); 7.8–8.1 (m, 3H); 8.6 (d, 1H). |
| (k) S(+)-enantiomer; $\alpha_D^{20}$ (hydrochloride) +22.6 (c = 1; CH$_3$OH) |

TABLE 2

Compounds of the general formula (II)

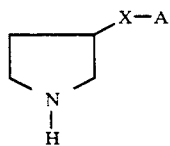

| Ex. | —X—(A) | —A | $R_f$/Solvent[a] | Salt[b]/Melting point (°C.) | prepared from |
|---|---|---|---|---|---|
| 48 | —O— | Phenyl | | [cf. DE 19 64 511] | |
| 49 | —OCH$_2$— | Phenyl | 0.41 (TET) | Cl; Syrup | Ex. 71 |
| 50 | —O— | 2-Methoxyphenyl | | [cf. U.S. Pat. No. 430 60 65] | |
| 51 | —O— | 3-Methoxyphenyl | | [cf. DE 19 64 511] | |
| 52 | —O— | 2-cyanophenyl | 0.35 (TET) | F; Syrup[c] | Ex. 72 |
| 53 | —O—[c] | 2-Carbamoylphenyl | | [cf. DE 19 64 510] | |
| 54 | —O— | (1-Cyano)naphth-2-yl | 0.11 (DM) | Cl; 204–208 | Ex. 70 |
| 55 | —O— | 2-Methoxyphenyl | [f] | — | Ex. 74 |
| 56 | —O— | (2-Carbamoyl)-naphth-1-yl | <0.1 (TET) | Cl; [g] | Ex. 75 |
| 57 | —O— | Naphth-1-yl | 0.42 (TET) | Cl; 223–226 | Ex. 77 |
| 58 | —O— | Naphth-2-yl | 0.5 (TET) | Cl; 168–170 | Ex. 78 |
| 59 | —OCH$_2$— | Naphth-1-yl | 0.25 (TET) | Cl; 117–124 | Ex. 69 |
| 60 | —OCH$_2$— | Naphth-2-yl | 0.28 (TET) | Cl; 128–130 | Ex. 79 |
| 61 | —OCH$_2$— | 2-Fluorphenyl | 0.5 (TET) | Cl; Syrup | Ex. 80 |
| 62 | —O— | (1-Methyl)-indol-4-yl | <0.1 (TET) | Cl; Syrup[h] | Ex. 81 |
| 63 | —O— | 4-Methoxyphenyl | | [compare J. Med. Chem. 12, 435 (1969)] | |
| 64 | —O— | 5,6,7,8-Tetra-hydro-naphth-1-yl | 0.52 (TET) | Cl; 196–200 | Ex. 83 |
| 65 | —O— | Quinolin-2-yl | 0.42 (TET) | [i] | Ex. 84 |
| 66 | —O— | Isoquinolin-1-yl | 0.38 (TET) | Cl; foam | Ex. 85 |
| 67[k] | —O— | 2-Methoxyphenyl | 0.22 (TET) | Cl; 145–147 | Ex. 86 |
| 68 | —O— | 2-(Prop-2-en-1-yl-oxy)phenyl | 0.2 (TET) | Cl; Syrup | Ex. 87 |

EXAMPLE 69

1-tert.Butoxycarbonyl-3-(1-naphthyl)methoxy-pyrrolidine

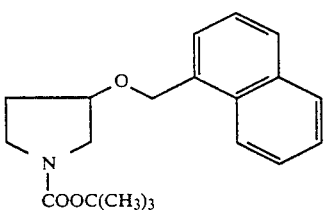

1.27 g of an 80% strength suspension of sodium hydride in paraffin (44 mmol) were added in small portions at 0° C. to a solution of 7.49 g (40 mmol) of 1-tert.butoxycarbonyl-3-hydroxy-pyrrolidine in 40 ml of dry dimethyl sulphoxide. 7.77 g (44 mmol) of 1-chloromethyl-naphthalene were subsequently slowly added dropwise. After 3 hours at room temperature, the mixture was poured into 200 ml of saturated ammonium chloride solution, extracted a number of times using ether, dried (MgSO$_4$) and concentrated. Flash chromatography (petroleum ether-toluene, then toluene-ethyl acetate gradients) gave 10.5 g of the title compound (76%) as a yellowish oil.

$R_f$=0.46 (toluene-ethyl acetate 3:1)

EXAMPLE 70

1-tert.Butoxycarbonyl-3-[(1-cyano)-2-naphthyloxy]pyrrolidine

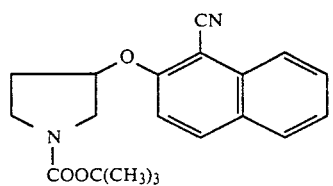

7.66 g (44 mmol) of diethyl azodicarboxylate in 20 ml of dry tetrahydrofuran were added dropwise at 0° C. to a solution of 6.2 g (37 mmol) of 1-cyano-2-hydroxy-naphthalene, 8.2 g (44 mmol) of 1-tert.butoxycarbonyl-3-hydroxy-pyrrolidine and 11.5 g (44 mmol) of triphenylphosphine in 100 ml of dry tetrahydrofuran. After 2 hours at room temperature, the mixture was concentrated and the residue was purified twice by flash chromatography (toluene-ethyl acetate gradient). 7.3 g of a reddish oil, which was brought to crystallization by trituration with ether, were obtained.

Yield: 4.7 g (40%)

Melting point: 145°–148° C.

$R_f$=0.33 (toluene/ethyl acetate 3:1, silica gel plates)

EXAMPLES 71 TO 87

Examples 71 to 87 are summarized in Table 3; they are obtained analogously to Examples 69/70.

Legend to Table 3

(a) Abbreviations used:
    BN = phenylmethyl
    BOC = tert.butoxycarbonyl
(b) Unless stated otherwise, the products occurred as oils.
    Abbreviations used for the TLC systems: silica gel plates, eluent TE 31 = toluene/ethyl acetate 3:1
    TE 11 = toluene/ethyl acetate 1:1
    TM 41 = toluene/methanol 4:1
(c) Abbreviations used:
    X = 1-tert.butoxycarbonyl-3-hydroxy-pyrrolidine (obtained by reaction of 3-hydroxypyrrolidine with di-tert.butyl pyrocarbonate in tetrahydrofuran/methanol 5:1)
    A has the meaning indicated in column "A"
(d) (−)-Enantiomer; $D^{20}$ = −6.8 ($CH_3OH$; c = 0.93)
(e) (−)-1-Benzyl-3-hydroxy-pyrrolidine [J. Med. Chem. 29, 2504 (1986)].
(f) Reaction of Example 76 with ammonia (gaseous) in ethanol at 0°C. to room temperature.
(g) Still contains unreacted 2-naphthol; further reacted as a mixture.
(h) Reaction of Example 82 with dimethyl sulphate and sodium hydride in dimethylformamide at 0° C. → room temperature.
(i) Melting point 160–162° C.
(k) Silica gel plates; eluent = ethyl acetate; MS (m/e) = 314, 257, 241, 169
(l) Carried out in THF/acetonitrile 1:2.5 at 40° to 50° C.
(m) S(+)-enantiomer; $α_D^{20}$ = +32.4 (c = 1; $CH_3OH$)
(n) R(−)-1-tert.-butoxycarbonyl-3-hydroxy-pyrrolidine [$α_D^{20}$ = −25.4 (c = 1; $CH_3OH$)]. Heterocycles 1987, 2247;

TABLE 3

Compounds of the general formula (IV)

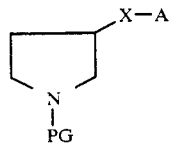

| Ex. | —X—(A) | —A | PG[a] | R_f/Solvent[b] | Prepared from |
|---|---|---|---|---|---|
| 71 | —OCH₂— | Phenyl | BOC | 0.49 (TE 31) | X + A—CH₂Br |
| 72 | —O— | 2-Cyanophenyl | BOC | 0.27 (TE 31) | X + A—OH |
| 73 | —O— | (2-Methoxy-6-cyano)-phenyl | BOC | 0.42 (TE 31) | X + A—OH |
| 74[d] | —O— | 2-Methoxyphenyl | BN | 0.38 (TE 11) | [e] + A—OH |
| 75 | —O— | (2-Carbamoyl)-naphth-1-yl | BOC | 0.3 (TM 41) | Ex. 76 + NH₃[f] |
| 76 | —O— | (2-Phenoxycarbonyl)-naphth-1-yl | BOC | 0.46 (TE 31) | X + A—OH |
| 77 | —O— | Naphth-1-yl | BOC | 0.63 (TE 31) | X + A—OH |
| 78 | —O— | Naphth-2-yl | BOC | 0.6[g] (TE 31) | X + A—OH |
| 79 | —OCH₂— | Naphth-2-yl | BOC | 0.43 (TE 31) | X + A—CH₂Cl |
| 80 | —OCH₂— | 2-Fluorphenyl | BOC | 0.48 (TE 31) | X + A—CH₂Br |
| 81 | —O— | (1-Methyl)indol-4-yl | BOC | 0.48 (TE 31) | Ex. 82 + (CH₃)₂SO₄[h] |
| 82 | —O— | Indol-4-yl | BOC | 0.42 (TE 31)[i] | X + A—OH |
| 83 | —O— | 5,6,7,8-Tetrahydro-naphth-1-yl | BOC | 0.58 (TE 31) | X + A—OH |
| 84 | —O— | Quinolin-2-yl | BOC | 0.87[k] | X + A—OH |
| 85 | —O— | Isoquinolin-1-yl | BOC | 0.58 (TM 41) | X + A—OH[l] |
| 86[m] | —O— | 2-Methoxyphenyl | BOC | 0.49 (TE 31) | [n] + A—OH |
| 87 | —O— | 2-(Prop-2-en-1-yloxy)-phenyl | BOC | 0.52 (TE 31) | X + A—OH |

USE EXAMPLE

EXAMPLE 69

Affinity for the 5-HT₁ receptor

The high affinity of the compound according to the invention for 5-hydroxytryptamine receptors of the subtype 2 is represented by way of example in Table 4. The values indicated are data which have been determined from receptor binding studies using calf hippocampus membrane preparations. For this purpose, ³H-serotonin was used as a radioactively labelled ligand.

TABLE 4

| Compound from Example No. | Ki (nmol/l) |
|---|---|
| 1 | 2 |
| 6 | 9 |
| 8 | 1.3 |
| 10 | 6 |
| 19 | 7 |
| 23 | 0.3 |

Comparison

In DE-A 1,964,511 pyrrolidines with
A equal to o-methoxy-phenyl,
X equal to oxygen,
B equal to 2-propyl and
n equal to 0
were described.

This compound has a Ki value of 1.0 μmol/l.

It is understood that the specification and examples are illustrative but not limitative of the present invention and that other embodiments within the spirit and scope of the invention will suggest themselves to those skilled in the art.

We claim:

1. A 1,3-disubstituted pyrrolidine of the formula

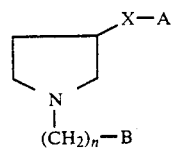

(I)

wherein
A stands for phenyl, naphthyl, furan, thiophene, isoxazole, pyridine, pyrimidine, indole, indazole, benzofuran, benzoxazole, quinoline, isoquinoline tetralin, indene, chroman, dihydrobenzodioxin, dihydroindole, tetrahydroquinoline or dihydrobenzofuran, which are optionally mono- or disubstituted by identical different C$_1$-C$_4$-alkyl, C$_1$-C$_4$-alkoxy, C$_1$-C$_4$-alkoxy carbonyl, C$_2$-C$_4$-alkenyloxy, acetyloxy, benzoyloxy, cyano, phenyl, benzyl, sulfonylamino (C$_1$-C$_6$), sulfamoyl, carbamoyl, carbonylamino, fluorine, chlorine, bromine, trifluoromethyl, trifluoromethoxy or difluoromethoxy, X stands for —O—CH$_2$—, —CH$_2$—O— or —O—, B stands for a group of the formula

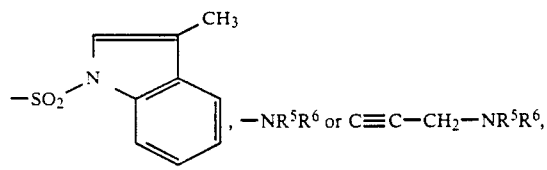

, —NR$^5$R$^6$ or C≡C—CH$_2$—NR$^5$R$^6$,

R$^5$ and R$^6$ together with the nitrogen atom form a ring selected from the group consisting of

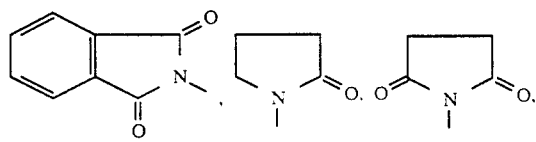

and

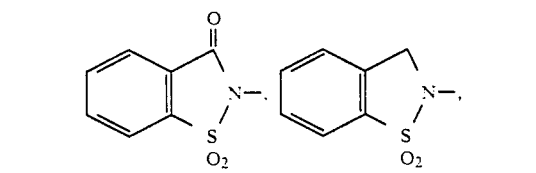

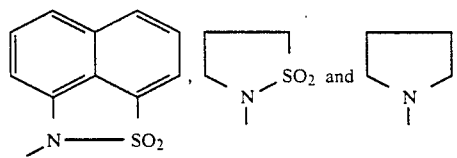

n stands for a number from 1 to 6 or salt thereof.

2. A compound according to claim 1 wherein such compound is 3-(2-cyanophenoxy)-1-[4-(1,1-dioxido-3-oxo-2,4-dihydrobenzisothiazol-2-yl)butyl]-pyrrolidine of the formula

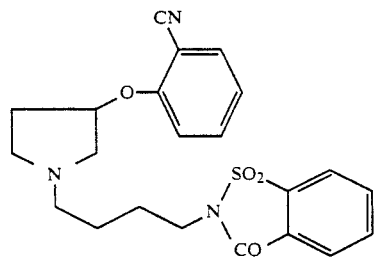

or a salt thereof.

3. A compound according to claim 1, wherein such compound is 3-(2-methoxyphenoxy)-1-[4-(1,1-dioxido-3-oxo2,4-dihydrobenzisothiazol-2-yl)butyl]-pyrrolidine of the formula

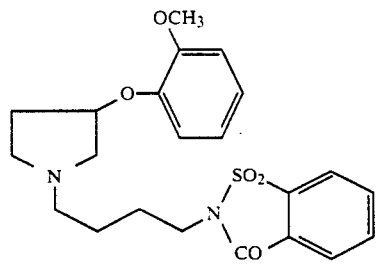

or a salt thereof.

4. A compound according to claim 1, wherein such compound is 3-[2-(napth-1-yl-oxy)]-1-[4-(1,1-dioxido-3-oxo-2,4-dihydrobenzisothiazol-2-yl) butyl]-pyrrolidine of the formula

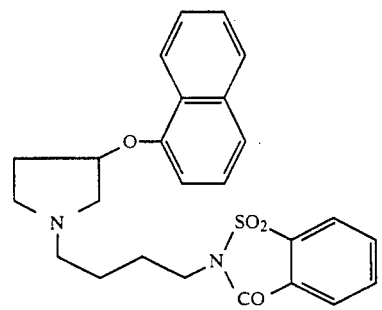

or a salt thereof.

5. A compound according to claim 1, wherein such compound is R(—)-3-(2-methoxy-phenoxy)-1-[4-(1,1-dioxido-3-oxo-2,3-dihydro-benzisothiazol-2-yl)butyl]-pyrrolidine

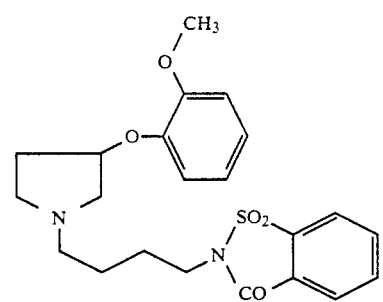

or a salt thereof.

6. A composition active on the central nervous system comprising an amount effective therefor of a compound or salt according to claim 1 and a diluent.

7. A composition according to claim 6 in the form of a tablet, capsule or ampule.

8. A method of treating the central nervous system of a patient in need thereof which comprises administering to such patient an amount effective therefor of a compound or salt according to claim 1.

9. The method according to claim 8, wherein such compound is
1,3-disubstituted pyrrolidine, 3-(2-cyanophenoxy)-1-[4-(1,1-dioxido-3-oxo-2,4-dihydrobenzisothiazol-2-yl)butyl]-pyrrolidine, 3-(2-methoxyphenoxy)-1-[4-(1,3-dioxido-3-oxo-2,4-dihydrobenzisothiazol-2-yl)butyl]-pyrrolidine, 3-[2-(napth-1-yl-oxy)]-1-[4-(1,1-dioxido-3-oxo-2,4-dihydrobenzisothiazol-2-yl)butyl]-pyrrolidine or R(—)-3-(2-methoxy-phenoxy)-1-[4-(1,1-dioxido-3-oxo-2,3-dihydro-benzisothiazol-2-yl)butyl]pyrrolidine or a salt thereof.

* * * * *